United States Patent [19]

Nelson et al.

[11] Patent Number: 4,889,133
[45] Date of Patent: Dec. 26, 1989

[54] METHOD FOR NONINVASIVE BLOOD-PRESSURE MEASUREMENT BY EVALUATION OF WAVEFORM-SPECIFIC AREA DATA

[75] Inventors: Craig H. Nelson, Hillsboro; Thomas J. Dorsett, Hillsboro; Charles L. Davis, Portland, all of Oreg.

[73] Assignee: Protocol Systems, Inc., Beaverton, Oreg.

[21] Appl. No.: 198,468

[22] Filed: May 25, 1988

[51] Int. Cl.$^4$ ............................................... A61B 5/02
[52] U.S. Cl. .................................................... 128/681
[58] Field of Search ................................. 128/680–685

[56] References Cited

U.S. PATENT DOCUMENTS

| | | |
|---|---|---|
| 3,903,872 | 9/1975 | Link . |
| 4,009,709 | 3/1977 | Link et al. . |
| 4,074,711 | 2/1978 | Link et al. . |
| 4,105,021 | 8/1978 | Williams et al. ............... 128/683 |
| 4,154,238 | 5/1979 | Link . |
| 4,263,918 | 4/1981 | Swearingen et al. . |
| 4,271,844 | 6/1981 | Croslin . |
| 4,349,034 | 9/1982 | Ramsey, III . |
| 4,360,029 | 11/1982 | Ramsey, III . |
| 4,407,297 | 10/1983 | Croslin . |
| 4,461,266 | 7/1984 | Hood, Jr. et al. . |
| 4,592,365 | 6/1986 | Georgi ............................ 128/680 |
| 4,597,393 | 7/1986 | Yamakoshi et al. . |
| 4,638,810 | 1/1987 | Ramsey, III et al. . |
| 4,699,152 | 10/1987 | Link . |
| 4,703,760 | 11/1987 | Miyawaki et al. .............. 128/681 |
| 4,751,930 | 6/1988 | Terada et al. .................. 128/681 |
| 4,776,344 | 10/1988 | Shirasaki et al. ............... 128/681 |

Primary Examiner—Francis Jaworski
Attorney, Agent, or Firm—Kolisch, Hartwell & Dickinson

[57] ABSTRACT

A microprocessor-controlled, oscillometric method for determining a patient's systolic, diastolic, and mean arterial pressure, practiced in a system comprising an inflatable, occluding cuff, a pump and a valve coupled to the cuff, and monitoring apparatus coupled to the cuff adapted to measure cuff pressure and recurring blood-pressure pulsations occurring in the cuff that are caused by each heart contraction occurring in a measurement cycle. Cuff pressure is raised to a level above the patinet's systolic pressure, and progressively reduced in a stepwise fashion to an ending cuff pressure. A fixed number of pulsations are measured and processed at a first and second cuff-pressure step, and a generally lesser number of oscillations are measured and processed at a third and subsequent cuff-pressure steps. The method includes a first artifact rejection technique used to check for false data relative to the formation of each blood-pressure pulsation. Further, the method includes calculating, for each blood-pressure pulsation, the impulse of a force that is exerted upon the patinet's blood from, and during, each heart contraction that occurs in the measurement cycle. An impulse value is stored relative to each pulsation. A second artifact rejection technique is used, beginning at the second cuff-pressure step, to generate a prediction curve for predicting a next, expected-to-be-stored pulsation impulse value for a next, lower cuff-pressure step. The second artifact rejection technique is also used to repeatedly smooth the prediction curve based on the difference between a pulsation's calculated impulse value and its respective predicted impulse value. A final, smoothed curve is generated reflecting a final impulse value for each cuff-pressure step. From the final curve, the desired blood pressure parameters are derived and displayed in the form of arabic numerals by means of an LCD readout.

20 Claims, 7 Drawing Sheets

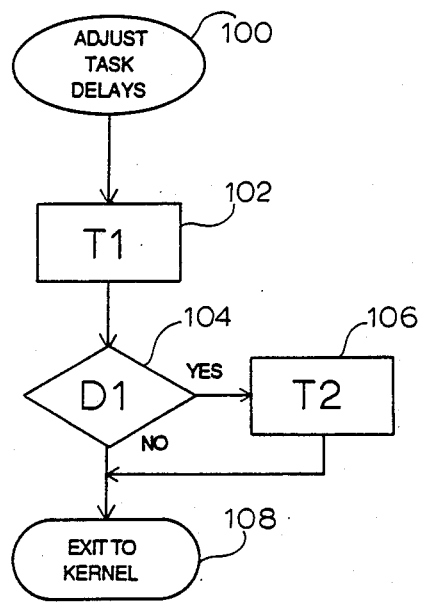
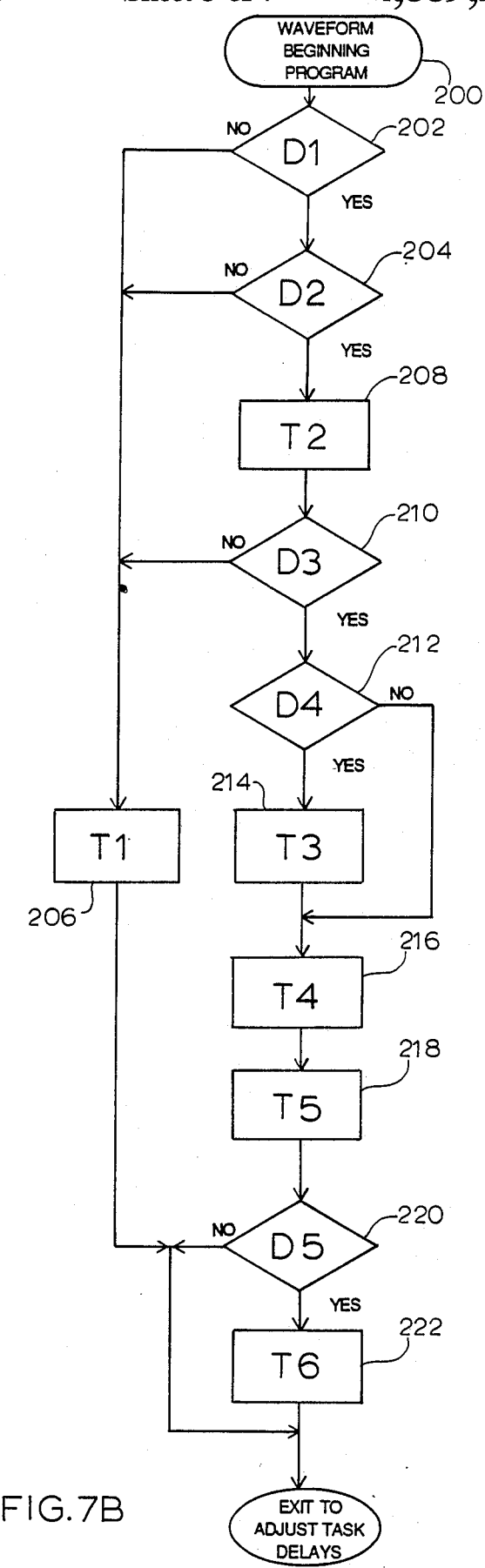
FIG.7A
FIG.7B

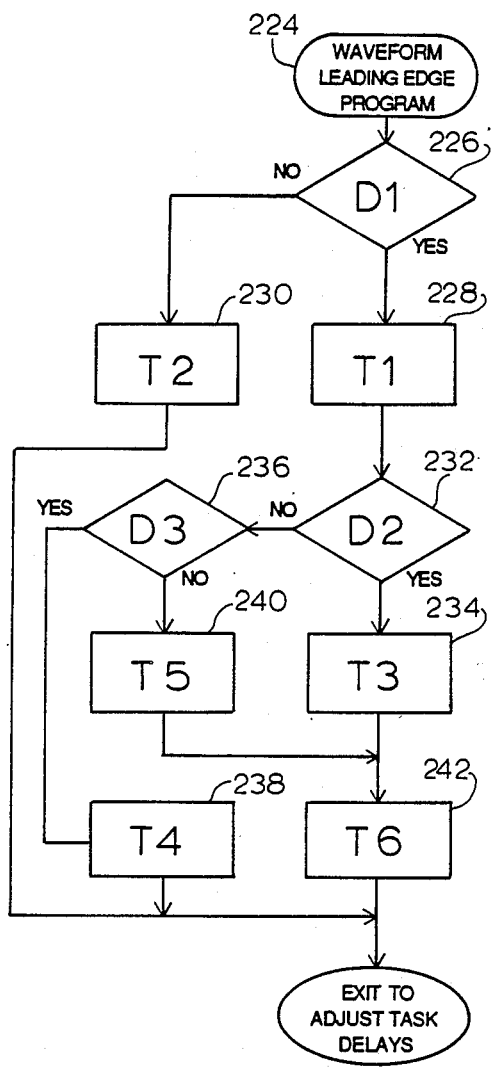
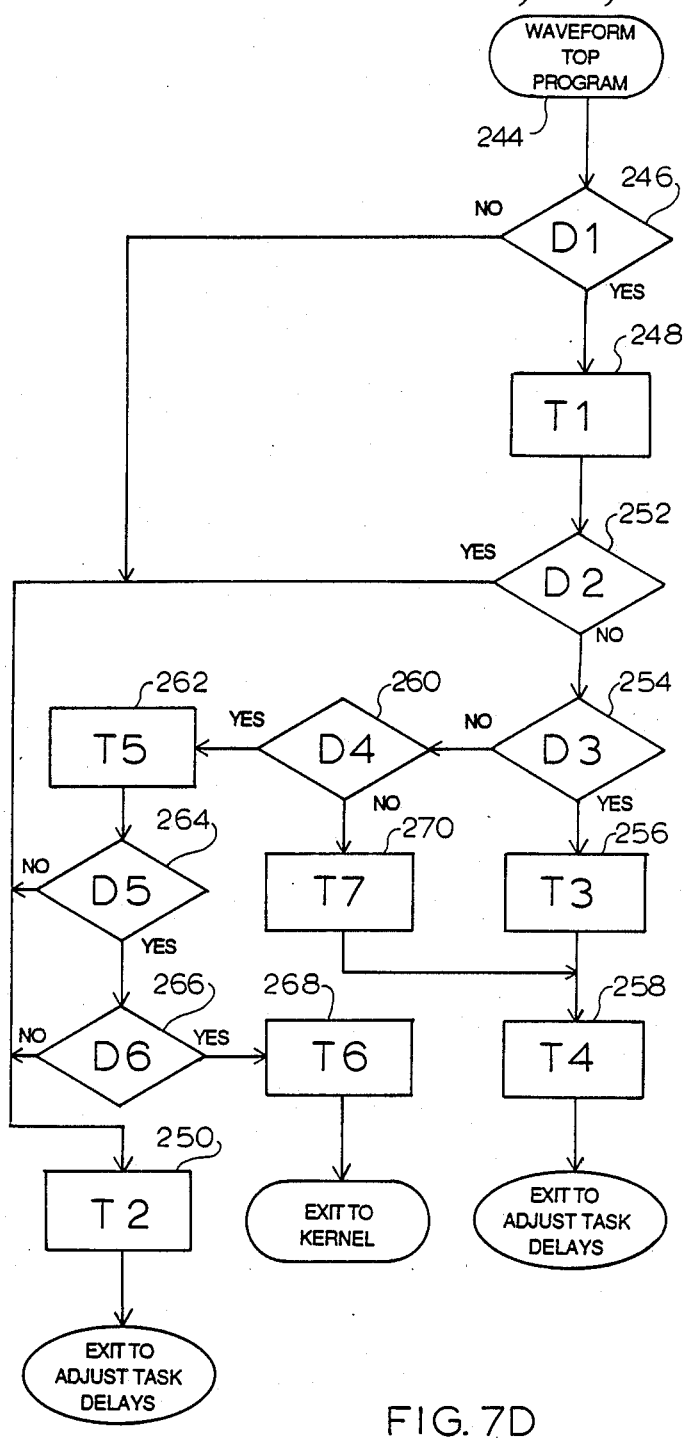
FIG. 7C
FIG. 7D

METHOD FOR NONINVASIVE BLOOD-PRESSURE MEASUREMENT BY EVALUATION OF WAVEFORM-SPECIFIC AREA DATA

BACKGROUND AND SUMMARY OF THE INVENTION

This invention pertains to an improvement of the oscillometric method for noninvasive blood-pressure measurement, and more particularly to a unique application for microprocessor-controlled blood-pressure monitoring.

Examples of noninvasive blood-pressure measurement methods in the closest prior art are disclosed in U.S. Pat. Nos. 4,461,266 to Hood, et al. and 4,638,810 to Ramsey.

In the typical practicing of an oscillometric, noninvasive blood-pressure measurement method with a person, a counterpressure-producing cuff is wrapped around the person's upper arm, with the cuff then inflated to a counterpressure above systolic pressure to occlude a artery (blood vessel) in the arm. Thereafter cuff counterpressure is progressively reduced in a stepped fashion from this suprasystolic pressure to an ending counterpressure where the cuff is substantially deflated. During progressive reduction of cuff counterpressure, the artery opens progressively from an occluded state to an unoccluded state.

During the change from the occluded state to the unoccluded state, the artery begins to pulsate against the cuff, and the waveforms of these pulsations are monitorable to produce graphic illustrations of blood-pressure parameters. As is well-known to those skilled in the art in handling blood-pressure measurements, the pulsations just referred to increase in amplitude toward a maximum as cuff counterpressure decreases below systolic pressure, and then decrease in amplitude. By categorizing these pulsations relative to their occurrences in time and to their respective amplitudes, desired blood-pressure parameters are determined.

Explaining the significant monitored heart activity with a little more particularity, during each heart contraction, a force is exerted upon the blood in the vascular system. During the time that this force is active, the blood is accelerated, or given momentum. The integral of this force with respect to time (when the force is active) is called the "impulse" of the force, with "impulse" bearing the same units as momentum. Accordingly, if the instantaneous pressure in the cuff is monitored during a measurement procedure, and integrated over the time during which measurements are being made, it is possible to develop a data quantity that is directly proportional to impulse—that characteristic of blood flow from which, it turns out, the most accurate blood-pressure data can be derived.

A critical determination is that of mean arterial pressure (MAP). It is from this determination that systolic and diastolic pressures are calculated. Typically, MAP has been defined according to the prior art as the pressure in the cuff where blood-pressure pulsations have the largest amplitudes. Amplitude data, however, does not relate well to the characteristic described above as impulse, and, because pulsation impulse data is, for the sake of ultimate accuracy, the most desirable data, it does not reliably produce the most accurate ultimate information.

The method of the present invention significantly addresses this issue.

Another consideration is that conventional blood-pressure measuring methods typically reduce counterpressure, progressively, in steps at a relatively slow rate. This results in a relatively long time period for an entire measurement cycle, and often as a consequence, patient discomfort.

Finally, in all methods of acquiring usable blood-pressure data, it is important to detect, and reject, as faithfully as possible, pressure "artifacts" which are not induced by blood-pressure pulsations. Artifacts occur, for example, where a subject moves, changes muscle tension, etc.

An important object of the present invention, accordingly, is to categorize blood-vessel pulsations in a far more accurate manner by a value that more closely approximates blood-vessel pulsation impulse.

Another object of the invention is to provide for artifact rejection in a unique way which ensures that accepted pressure waveforms truly are blood-pressure induced.

A further object is to decrease the number of pressure waveforms that are monitored at each cuff counterpressure level, thereby to decrease the overall time period of a measuring cycle, thus to minimize subject discomfort. The method of the present invention, which might be thought of as an "impulse-based method", offers a significant improvement over the closest prior art because, inter alia, it defines the blood-pressure pulsation which corresponds to MAP as that pulsation which produces a waveform having the greatest area, as distinguished from that having the greatest amplitude—area being a direct indication of impulse. Such waveform area data is an indicator of MAP which for many reasons is more accurate than waveform amplitude data.

Another extremely important consideration is that where waveform area (impulse) data forms the foundation for the determination of MAP, systolic pressure and diastolic pressure, signal-to-noise problems are greatly reduced.

For all of the important reasons given above, the desired blood-pressure parameters of a subject, determined in accordance with the present invention, have improved accuracy over the same parameters determined in accordance with the closest prior art.

To deal with the issue of false "artifact" data, the invention employs two different artifact-rejection techniques, during two different phases of a blood-pressure measuring cycle, to assure that developed waveform area data accurately and reliably represents blood-pressure-induced changes in the occluding cuff.

The first artifact-rejection technique verifies that monitored pressure signal data corresponding to pressure waveforms is blood-pressure induced.

A second artifact-rejection technique verifies that developed area data values are also blood-pressure induced. This second technique, after development of waveform area-data values for a predetermined number of cuff counterpressure levels at the beginning of a measuring cycle, predicts a next, expected-to-be-encountered area-data value for the next, lower cuff counterpressure level. Employing prediction for successive, next, lower cuff counterpressure levels, provides a simple and accurate method of artifact rejection that substantially decreases the number of pressure waveforms required to be monitored at a given cuff counterpressure level. Therefore, if a next, developed waveform area-data value for a measured waveform is within experimentally set upper and lower bounds of its corresponding predicted value, the measured value is accepted as being blood-pressure induced.

This important feature of area-data acquisition, coupled with on going next-to-be-expected value prediction, significantly enhances the likelihood that a false data pulse will be rejected as an artifact.

Using the prediction technique just described for subsequent cuff counterpressure levels, it will generally be necessary to monitor only one pressure waveform at a given cuff counterpressure level. As will be explained, if the first pressure waveform which is monitored does not have an area-data value that is within the upper and lower bounds of its corresponding predicted value, subsequent waveforms will be monitored until one is found which does meet the boundary conditions. This situation, of "looking" for successive, subsequent "boundary-meeting" waveforms, continues only for a predetermined ultimate time interval, after which, if no proper waveform is found, the method of the invention aborts the measurement cycle.

In addition, and further in accordance with special features of the invention, the second artifact-rejection technique adjusts previously encountered (and stored) waveform area-data values based on the difference between a measured waveform area-data value and a corresponding predicted waveform area-data value for a given cuff counterpressure level. This is referred to herein as a "smoothing" technique. By adjusting previously stored values, this second technique provides further ensurance of the accuracy of ultimately derived, desired blood-pressure parameters.

These and other objects and advantages which are attained by the invention will become more fully apparent as the description that now follows is red in conjunction with the accompanying drawings and computer program flow charts.

DESCRIPTION OF THE DRAWINGS

FIGS. 7A-7D, inclusive, are computer-program flow charts illustrating computer-based implementation of a portion of the method of the present invention.

DETAILED DESCRIPTION OF THE PREFERRED MANNER OF PRACTICING THE INVENTION

Before describing the present invention in detail, reference is made selectively to FIGS. 1-4 in order to illustrate generally an important difference between the method of this invention for noninvasive blood-pressure monitoring involving waveform area data, and the closest prior art method which involves waveform amplitude data.

Figure 1:
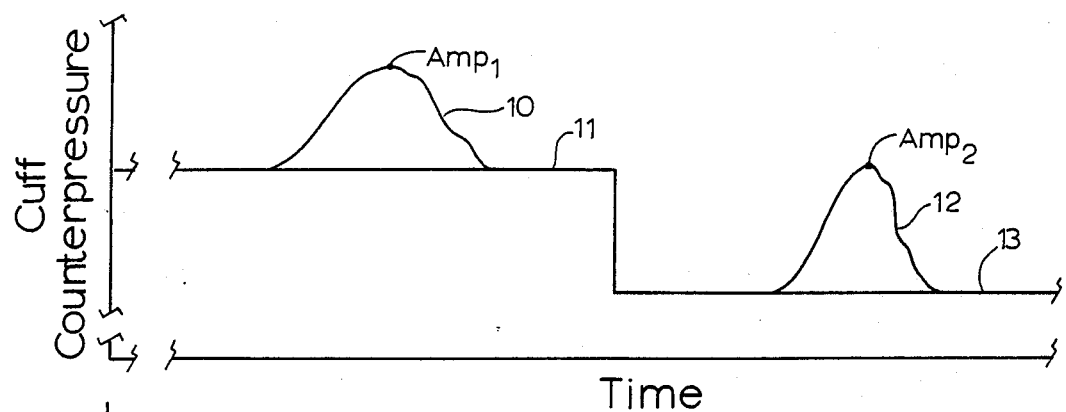
FIG. 1 is a fragmented graph of cuff counterpressure decreasing over time, showing two cuff counterpressure levels with blood-pressure-induced waveforms to illustrate amplitude data being employed, according to the closest prior art, in the derivation of the usual, desired parameters of MAP, systolic pressure and diastolic pressure.
Figure 3:
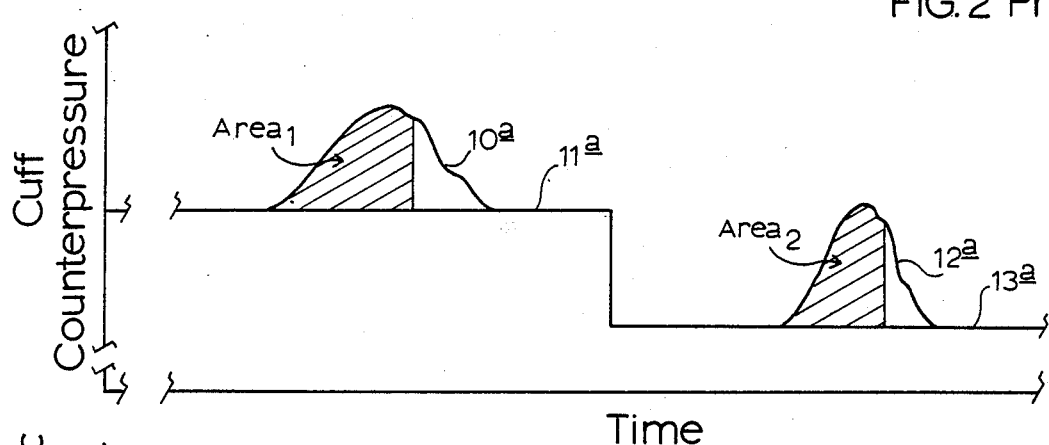
FIG. 3 is like FIG. 1, except that it helps to illustrate the more accurate derivation of desired parameters from waveform area (impulse) data acquired according to the method of the present invention.

FIGS. 1 and 3 illustrate identically, two successive blood-pressure waveforms which have been acquired during the performance of a blood-pressure monitoring cycle. The waveforms illustrated in FIG. 1 have been acquired by a system which employs the above-mentioned prior art technique of peak amplitude monitoring. The waveforms illustrated in FIG. 3 have been acquired in a system employing the method of the present invention, wherein waveform area data is employed in the derivation of the desired parameters. The waveforms illustrated in FIGS. 1 and 3 are shown as matching duplicates, in order to illustrate one of the key differences between the derivation of desired parameters according to the prior art and that according to the method of the invention.

Figure 2:
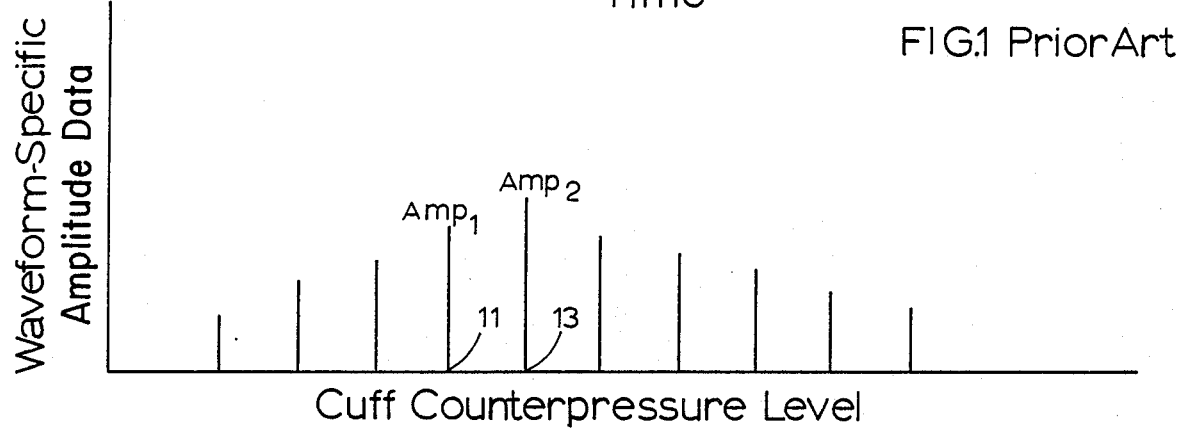
FIG. 2 is a graph of waveform-amplitude data, such as that illustrated in FIG. 1, acquired over an entire measurement cycle of a test subject.
Figure 4:
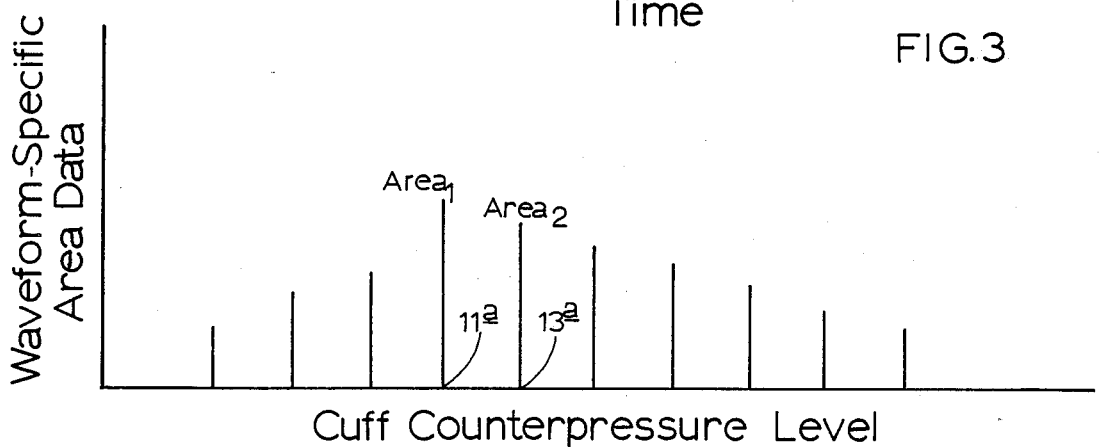
FIG. 4 is like FIG. 2, except that, as will be explained, what it shows is based on waveform area (impulse) data noted over an entire measurement cycle.

FIG. 2 illustrates conventional waveform amplitude data forming a conventional data envelope from which, according to the closest prior art technique, MAP, systolic pressure and diastolic pressure are determined. FIG. 4 is similar in appearance except that it illustrates waveform area data forming a unique data envelope, according to the present invention, from which these three desired parameters are more accurately derived.

Turning attention specifically to FIG. 1, there are shown two blood-pressure-induced pressure waveforms 10, 12 occurring at cuff counterpressuee levels 11, 13, respectively, during a blood-pressure measurement cycle. FIG. 1 is a fragmented graph specifically showing cuff counterpressure levels 11, 13 as occurring in the time period of the measurement cycle when blood-pressure pulsations are at maximum strengths.

According to the method of the closest prior art, and as is depicted in FIG. 1, amplitudes $Amp_1$, $Amp_2$ of waveforms 10, 12, respectively, are "chosen" to be the acquired significant data relative to these two waveforms. As a consequence, according to the prior-art amplitude method, waveform 12 is the larger, important waveform because $Amp_2$ is greater than $Amp_1$.

Looking now at FIG. 2 wherein an overall amplitude data envelope representing an entire measurement cycle is depicted (by the peaks of the vertical lines, or spikes), the data acquired for calculation utilization according to the prior art from pulses 10, 12 in FIG. 1 is shown, at cuff pressures 11, 13, respectively, with spikes labeled $Amp_1$ and $Amp_2$. Deriving, for example, MAP from the data shown in FIG. 2, MAP would be defined as the cuff counterpressure (13) where $Amp_2$ occurred, because $Amp_2$ turned out to be the largest-amplitude pulse data acquired and stored. Systolic and diastolic pressures would then be calculated based upon this selection for determining MAP.

In contrast to the closest prior art as depicted in FIG. 1, FIG. 3 depicts how the present invention approximates blood-pressure pulsation impulse. Instead of looking for a waveforms maximum amplitude, the present invention looks for a waveforms area, at least, as will be explained, up to the point that the waveform reaches a maximum amplitude. Waveforms 10a, 12a, corresponding to waveforms 10, 12, respectively, are shown occurring at cuff counterpressure levels 11a, 13a, respectively.

The reason for undertaking waveform area calculation to at least, and preferably (as will be explained) to slightly beyond, the slightly-larger-than-half areas $Area_1$, $Area_2$ of waveforms 10a, 12a, respectively, is that our experience has shown that such information most accurately leads, in the shortest time, to calculation of the desired parameters. Going much beyond the peak amplitude points may be time-wasteful.

FIG. 4, with an understanding of the importance of looking at waveform area data, helps to show the increased accuracy in determining MAP that is possible according to the present invention. In FIG. 4, an entire cycle, or envelope, of waveform area data is plotted against cuff counterpressures that occur during the entire envelope. $Area_1$ and $Area_2$ are the waveform area data values of waveforms 10a, 12a of FIG. 3 that directly relate to blood-pressure pulsation impulse. According to the present invention's waveform area data method of determining MAP, MAP is the lowest cuff counterpressure having the greatest waveform area data value. Thus, cuff counterpressure 11a is chosen as the counterpressure approximating MAP because $Area_1$ is the greatest area value.

Therefore, because area data most accurately reflects pulsation impulse, the data of the envelope in FIG. 4 results in a different, and more accurate, measure of MAP than the measure of MAP obtained from the waveform amplitude data depicted in FIG. 2.

The improved accuracy offered by the method of the invention vis-a-vis prior art amplitude-based methods will be seen by those skilled in the art to be even more significant where very short-duration, large-amplitude, but low-area pulses enter the monitoring picture.

Figure 5:
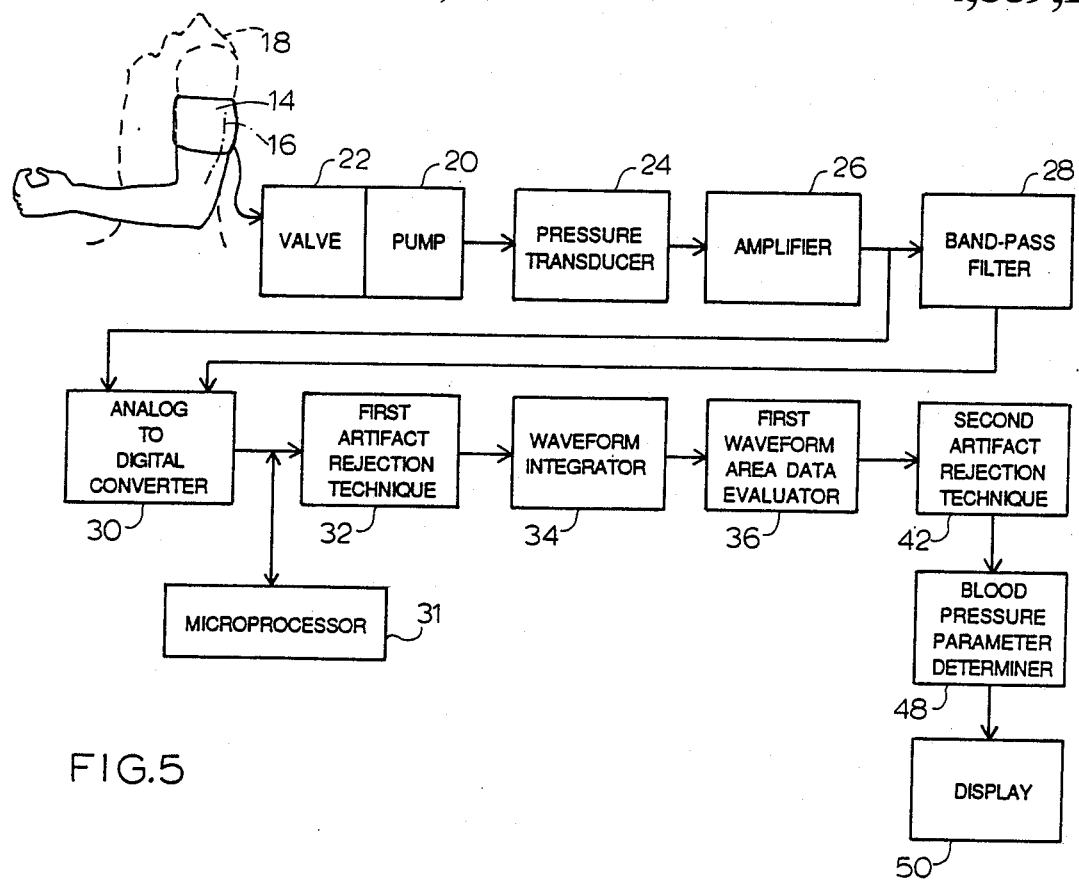
FIG. 5 is a schematic/block depiction of apparatus and software suitable for carrying out the present invention.

Turning now to FIG. 5, a schematic/block depiction of blood-pressure measuring apparatus and software characterizing the present invention is shown. Generally describing in operational steps and in descriptions of FIG. 5's contents what is "illustrated" by this figure, cuff 14 is a means for producing a baseline counterpressure, and is disposed adjacent a blood vessel 16 (wrapped around the arm) of a living subject 18. To begin a blood-pressure measuring cycle, a pump 20 inflates cuff 14 to a point where it exerts a counterpressure against the arm that is above systolic pressure, thereby occluding vessel 16.

Under the control of a microprocessor (still to be discussed), a valve 22 progressively reduces the cuff counterpressure from the beginning counterpressure level above systolic pressure to an ending counterpressure to be described later. Preferably, counterpressure is reduced in a stepwise fashion in order to monitor pressure changes occurring in cuff 14 at each step, or cuff counterpressure level. In the preferred practice of the invention cuff counterpressure reduces in steps of 5- to 6-mm Hg.

As the counterpressure in cuff 14 lowers, vessel 16 gradually begins to pulsate from heart contractions. More specifically, and as previously noted, these vessel pulsations are caused by blood that has been accelerated, or given momentum, during the time period of each successive heart contraction.

At each progressively reduced counterpressure level, a pressure transducer 24 receives, at a predetermined rate, an analog pressure signal composed of a cuff counterpressure component and a pressure pulsation component which "may be" blood-pressure-induced.

Transducer 24 converts each pressure signal into an electrical signal which is amplified by an amplifier 26. The amplified electrical signal is then sent to two different locations—a band-pass filter 28, and an analog-to-digital converter 30.

Each signal is sent to filter 28 in order to have the cuff counterpressure component filtered out. The signal output of filter 28 corresponds to pressure pulsations. From filter 28, the filtered signal component is fed to converter 30 from which there emerges a first stream of digitized data which corresponds to pressure pulsations. The presently preferred monitoring interval for transducer 24 is about 5.5-msec.

Each signal from amplifier 26 is also sent to converter 30 in order to provide a second stream of data corresponding to cuff counterpressure levels at which corresponding pressure pulsations occur. Technically, the signal from amplifier 26 contains both the cuff counterpressure component and the pressure pulsation component. However, because the pressure pulsation component's value is so small relative to the cuff counterpressure component's value, we have found that the signal from amplifier 26 substantially corresponds to cuff counterpressure.

Figure 6:
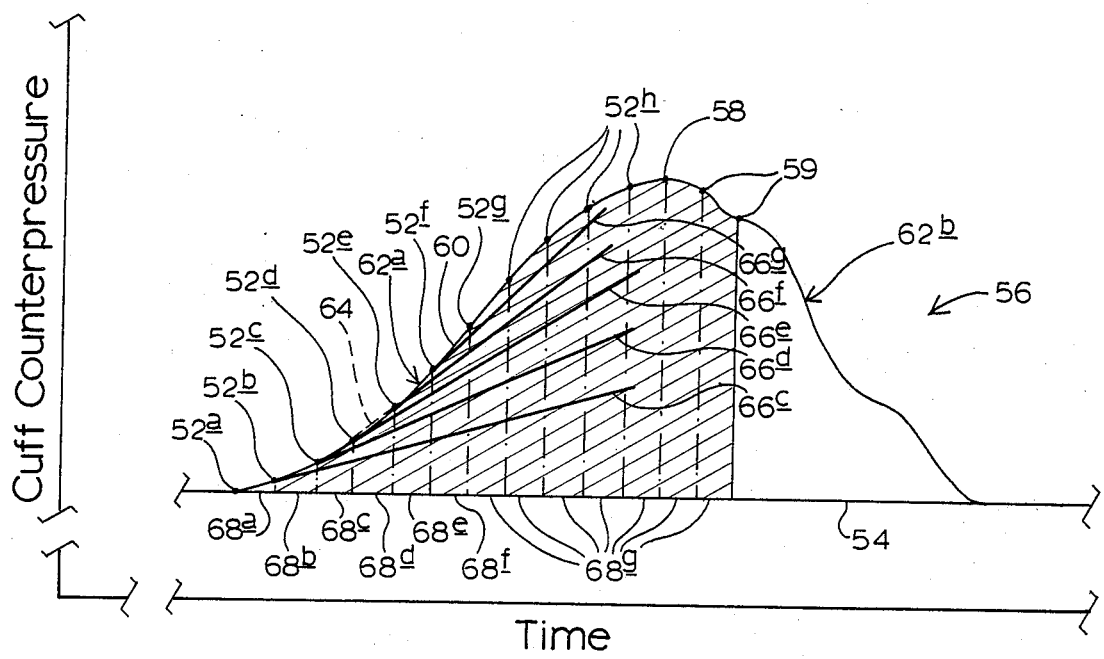
FIG. 6 is a fragmented graph of cuff counterpressure levels vs. time, showing one cuff counterpressure level, and also showing plural, time-successively-monitored blood-pressure-induced pressure signals that together form one blood-pressure-induced pressure waveform.

Hereafter, the second stream of data corresponding to cuff counterpressure levels will be called baseline counterpressure data, in order to assist the reader in understanding the method of the present invention that is graphically depicted in FIG. 6.

Thus, converter 30 digitizes two streams of data, one corresponding to baseline counterpressure data, and one corresponding to pressure pulsation data.

Data emanating from converter 30, is processed by a microprocessor 31 having suitable memory capacity—this microprocessor being operated by programs which will be described in the discussion of FIGS. 7A-7D and FIG. 9.

As an aid to understanding the description which follows, one should note that $Area_1$ and $Area_2$ of waveforms 10a, 12a, respectively, of FIG. 3 are graphic depictions of the waveform-specific area data which will shortly be described. Reference to graphic depictions of blood-pressure induced waveforms will be made throughout the remaining description.

Continuing the description of FIG. 5, pressure signal data from converter 30 are processed by microprocessor 31 in accordance with the important steps of the present invention. Most of the remaining blocks in FIG. 5 depict generally the software or program which directs the operation of the microprocessor.

In general terms the microprocessor examines the data streams arriving from converter 30 and, throughout the performance of a complete monitoring cycle of blood pressure, exercises various functions on this data to verify proper data, and to arrive at maximally accurate useful information. From an overview point of view, once a cycle of operation has begun, and particularly with the data streams emanating from the converter including pulsation data, and as cuff counterpressure is stepped downwardly as will be explained, every single pulsation which is sensed by the microprocessor has applied to it what is referred to herein as a first artifact rejection technique which is designed to determine that particular pulsation, or signal, is one which has been induced by blood-pressure activity. Throughout the cycle, every pulse which is so "validated" has an area integration performed with respect to it to develop waveform integrals upon which the microprocessor then performs other functions to arrive at the finally accepted and usable waveform-specific area data to produce an envelope such as that depicted in FIG. 4.

In accordance with the preferred manner of practicing the present invention, three waveforms (distinct groups of pulsation data) are accepted in each of the first two successively reduced counterpressure levels wherein pulses are detected and, as will be explained, a selection and averaging function is performed to select an acceptable, ultimately-generated-and-stored piece of waveform-specific area data. These two data, in such first two steps, establish, via operation of the microprocessor, a pattern for employing prediction, in accordance with what has been referred to herein as the second artifact rejection technique, as a way of determining whether subsequently acquired waveform-specific area data is or is not acceptable.

In FIG. 5, block 32 has been identified as the first artifact rejection technique as a way of putting an identifying name on that part of the program which looks at every single data stream reflecting a pressure pulsation to determine whether it is in fact a blood-pressure-induced pulsation. Block 34, identified as the waveform integrator, indicates that part of the program which, with regard to pulses accepted by block 32, performs a waveform area integration. Block 36, identified as the first waveform area data evaluator, represents that part of the program which examines the first two pulsation-data-containing counterpressure stepped levels for the purpose of "setting up" the operation of block 42—the second artifact rejection technique program. It is this program portion represented by block 42 which applies the second technique, including the generation of a prediction curve, the evaluation of waveform area data vis-a-vis its acceptability relative to that curve, and the smoothing of the curve referred to earlier.

Further, microprocessor 31 is directed by the second artifact rejection technique program to process the third and subsequent pulsation-data-containing counterpressure stepped-levels. At the end of the measuring cycle, the microprocessor generates a final curve connecting final, adjusted (by the aforementioned smoothing of the curve) waveform-specific area data for each counterpressure level of the measurement cycle. The second artifact rejection technique program directing the microprocessor during the third and subsequent counterpressure levels will be more fully described in the discussion of FIGS. 8A-8D, 9.

Still referring to FIG. 5, block 48 has been identified as the blood pressure parameter determiner as a way of putting an identifying name on that part of a program which directs the microprocessor to determine MAP, systolic, and diastolic pressure from the final curve of waveform-specific area data. The way in which the microprocessor determines the desired blood-pressure parameters from the final curve will be described in the discussion of FIG. 8D.

Finally, once the microprocessor has determined the desired blood pressure parameters, the parameters are sent in a digitized, arabic numeral form to a display 50 where the parameters are represented as arabic numerals by a conventional LCD read-out.

Referring now to FIGS. 6 and 7A-7D, first artifact rejection technique 32 will be more fully described. First, FIG. 6 shows a series of pressure signals (pulsation data) recurrently monitored by microprocessor 31 as pressure signal data 52a-52h, progressively diverging from a cuff counterpressure recurrently monitored as baseline counterpressure data shown by solid line 54. The baseline counterpressure data is shown as a solid line because cuff counterpressure remains relatively constant during the time period of monitoring depicted in FIG. 6.

FIG. 6 is fragmented to focus the reader on one baseline counterpressure data level, and the corresponding pressure signal data received and evaluated by first artifact rejection technique 32 at that level.

Generally, what the microprocessor is "looking" for, as it processes the two streams of data mentioned above, is the gradient change, relative to baseline counterpressure data, between successive pressure pulsation data points. If there is no false data present, as a wave begins, data points, with increasing gradients, will diverge from baseline data toward an inflection (reversing gradient) point. Thereafter, the gradients between successive data points will progressively decline. During this period of decreasing gradients, the data points will reach a maximum point of divergence from the baseline. Finally, the gradients will become negative after such maximum, and the data points will converge on the baseline.

The graphic depiction of one such waveform in FIG. 6, is shown to give one example of how the microprocessor, under the direction of software, processes pressure pulsation data in order to look for repeating waves of divergence-convergence relative to baseline data, to verify that each successive point of divergence is blood-pressure-induced, and to integrate each verified, blood-pressure-induced pulsation data value.

Pressure pulsation data 52a-52h are shown progressively diverging (with rising gradients) from baseline counterpressure data level 54 to a maximum point of divergence 58. Further, pulsation data 59 are shown progressively converging (with negative gradients) back to baseline 54. This divergence-convergence of pulsation data from baseline 54 is just one example of the aforementioned repeating waves of pulsation data divergence from, and then convergence on, baseline data.

The soon-to-be-described programs that direct microprocessor 31 as it "looks" for the occurrence of the aforementioned pulsation waves, characterizes the repeating pulsation data divergence-convergence relative to baseline data in three different phases of divergence-convergence. During each phase, the soon-to-bedescribed programs direct the microprocessor to use specific verification criteria for determining whether a pulsation data value is blood-pressure-induced.

The first phase of divergence corresponds to pulsation data that just begins to diverge from baseline data. In FIG. 6, this phase is represented by data 52a–52c. The second phase of divergence immediately follows the first phase and corresponds to pulsation data forming the leading edge of a waveform up to an inflection point of such leading edge. In FIG. 6, the pulsation data representing the second phase are data 52d–52g, wherein data 52g occurs at approximately an inflection point 60 of waveform 56.

The third phase corresponds to pulsation data progressively diverging from the waveform's inflection point, through a maximum point of divergence and to an ending point at which pulsation data begins converging back to baseline data. In FIG. 6, this third phase is represented by data 52h successively diverging from baseline 54 to a maximum point of divergence 58, and further, successively occurring data 59 which begins to converge back to baseline 54.

As previously mentioned, the microprocessor is directed by programs that carry out what has been referred to herein as a first artifact rejection technique designed to direct the microprocessor to verify that successively occurring pulsation data exhibiting the aforementioned three phases of amplitude divergence-convergence from baseline data are in fact blood-pressure-induced. Thus, if at any time the microprocessor receives a pulsation data value that does not meet the corresponding criteria (soon to be described), the microprocessor rejects the data value, and further rejects previously accepted data values that have exhibited the divergence-convergence phases. Then, the microprocessor "returns" to processing data at a zero point, or no divergence point, corresponding to baseline data.

Still looking at FIG. 6, the pulsation data on waveform 56 represent pulsation data that meet the verification criteria. Thus, upon receiving each successive pulsation data value, the microprocessor would continue "looking" for a subsequently occurring data value to verify that it is also blood-pressure induced. Only if a data value does not meet corresponding verification criteria, will the microprocessor stop "looking" for a next data value exhibiting one of the three aforementioned phases of divergence-convergence. Further, to make clear the repetitious nature of successive pulsation data divergence-convergence from baseline data, it is important to note that when the microprocessor stops "looking" and returns to a zero, no divergence point corresponding to baseline data, the microprocessor again repeats the verification process according to the first, second, and third phases as directed by software that is depicted and will be described in the description of FIG. 7A–7D.

Finally, it is important to note that microprocessor 31 is directed to perform an integration relative to each verified pulsation value.

During the first two phases of pulsation data divergence, the basic verification criterion used by the microprocessor is whether a gradient between a presently received value and a previous value is greater than a minimum gradient value. The complete criteria used in the verification process of the section of waveform 56 to the left of inflection point 60 will be more fully described in the discussion of the computer program flow charts of FIGS. 7A–7C.

As depicted in FIG. 6, and as an example of how each data value is verified, the microprocessor verifies that data value 52e results from a blood-pressure-induced signal by calculating a gradient 64 between data value 52e and previously received pressure data value 52d. If gradient 64 is greater than minimum gradient 66e, then signal data 52e is verified as resulting from a blood-pressure induced signal. Minimum gradient 66e is the gradient between data value 52d and 52c.

Further, as shown in FIG. 6, the minimum gradient criterion changes relative to an immediately previous gradient calculation. Thus, to verify data value 52f, the gradient between signal data 52e and 52f must be greater than newly adapted minimum gradient 66f (shown by solid line as an extension of previously-described, dotted-line 64) which is based on the gradient between signal data value 52d and signal data value 52e.

After the microprocessor verifies that a data value is blood-pressure induced, an integration is performed to develop the area under the curve which is forming, and successive integrated areas are summed All of this activity is undertaken by the waveform integrator part of the program represented by block 34 in FIG. 5.

Concerning the third phase, in order to verify that data is blood-pressure induced, the microprocessor does not use minimum gradient criteria. This is because gradients between successive pulsation values no longer successively increase during the third phase. From inflection point 60, gradients for subsequently-received data values will progressively decline until a zero gradient occurs at peak amplitude point 58. During this portion of data verification, if a gradient does not again increase over a previous gradient, an integration is performed relative to every data value.

From maximum amplitude point 58 on, the portion of the program represented by block 32 detects that the gradient between the next successive data values is negative. According to a preferred manner of practicing the invention, after maximum amplitude point 58, four data intervals are accepted and area integration takes place as before. The acceptance of these four additional intervals, along with the intervals leading up to the maximum amplitude point, provides not only a good database for the calculation of a figure strongly related to the actual area of the entire waveform, but also yields, under computer processing, a data figure which relates to overall pulse time period. Pulse time period is employed as yet another measure of the presence of an acceptable blood pressure induced pulse The microprocessor does not accept data beyond the four intervals just described in order to avoid the inadvertent acceptance of artifact data which might occur.

Turning now to FIGS. 7A–7D, four computer program flow charts are shown These programs direct microprocessor 31 to process the two streams of data discussed relative to FIGS. 5 and 6. Further, these programs direct the microprocessor to verify that every pulsation data value is blood-pressure induced. This verification has previously been described as first artifact rejection technique 32. Finally, these programs direct the integration and summing activities mentioned earlier as waveform integrator 34.

For each of the aforementioned three phases of divergence-convergence of pulsation data relative to baseline data, there is a corresponding phase of processing. The first concerns directing microprocessor 31 to verify data and to begin integration and summing when the data first begins to diverge from baseline counterpressure data. The program directing the microprocessor during this phase will be described in the discussion of FIG. 7B.

The second phase relates to data received after data first begins to diverge, and up to a point where data goes through an inflection point, such as point 60. The program that directs the microprocessor during this phase will be described in the discussion of FIG. 7C.

The third phase concerns data received after data goes through an inflection point through the maximum point of divergence and where pressure pulsation data begins to converge on baseline counterpressure. The program directing microprocessor 31 during this third phase will be described in the discussion of FIG. 7D.

The microprocessor, for these three phases, is directed by three computer programs in a specific order so that it can "track" a given waveform If at any time the verification criteria are not met for a presently received pulsation value, the microprocessor is directed to "return" to a "no divergence" status corresponding to baseline data. Then, the microprocessor is directed to repeat the three phases.

Included in the text of this specification are Tables I–V, inclusive. These tables contain identifying statements relative to designated blocks that appear in FIGS. 7A, 7B, 7C, 7D and 9, respectively.

In each of these figures, there are diamond-shaped decision blocks and rectangular-shaped task blocks. The decision blocks each pose a "question" which the microprocessor "answers" relative to a current data value. The answer will be either yes or no, and the program flow chart will contain additional decision blocks and task blocks for both possible responses to a question posed by a decision block. The task blocks either direct the microprocessor to perform a task, such as a gradient calculation or an integration, or direct it to leave a particular program and go to a different one.

The following table is a reference for the immediately-following description of FIG. 7A:

TABLE I

| | FIG. 7A |
|---|---|
| (D1) | Is Sample Counter Constant Met? |
| (T1) | Advance Sample Count |
| (T2) | Go to Program (X) |

Turning now to FIG. 7A, a flow diagram of an operations program, Adjust Task Delays 100, is shown that directs the microprocessor to leave one program and to go to another. As will become apparent in the discussion of FIGS. 7B–7D, any box referring to Adjust Task Delays 100 in the program flow chart depicted in FIGS. 7B, 7C and 7D means that the program continues through the program now being described.

First, task block 102 (T1) advances a data, or sample, counter by one increment. As is known generally in the art, sample counters are used in programming in order to allow a program to be referenced to real time. Thus, a programmer can use a sample counter together with a known time period between samples in order to limit the real time duration of a given program loop. Such sample counting is also present in the steps of the programs in FIGS. 7B–7D as a way for one program to be provided with a sample count criterion, which, when met will result in the program directing the microprocessor to leave the program and go to another desired program.

After performance by block 102 (T1), decision block 104 (D1) asks whether a previously programmed sample count constant has been met. If the sample count constant has been met, i.e., a given program has processed a preset amount of data, then block 106 (T2) says that a change of programs must occur (e.g. directing the microprocessor to go to a Program (X)). Then, the program exits to Kernel 108 with directions for microprocessor 31 to change to the specific program that block 106 (T2) requires.

If the answer to block 104 (D1) is no, then the program exits to Kernel 108 so that whatever program was in use before microprocessor 31 was directed to Adjust Task Delays 100, will continue to direct the microprocessor.

The following table is a reference for the immediately-following description of FIG. 7B:

TABLE II

| | FIG. 7B |
|---|---|
| D1 | Is Pulsation Value (N) ≧ Pulsation Value (N − 1)? |
| D2 | Is Pulsation Value (N) > baseline? |
| D3 | Is Gradient (N) > Minimum Gradient? |
| D4 | Is Program Count = First Count? |
| D5 | Is Program Count Constant Met? |
| T1 | Set Program Count = First Count |
| T2 | Calculate Pulsation Gradient (N) |
| T3 | Initialize Pulsation Value (N − 1) as Waveform Base; Set Integrator Counter = (N − 1) |
| T4 | Advance Program Counter by One Increment |
| T5 | Perform Waveform Integration |
| T6 | Go to Waveform Leading Edge Program; Set Program Count = 0 |

Turning now to FIG. 7B, Waveform Beginning Program 200 is shown. Decision block 202 (D1) asks whether pulsation value (N) is greater than or equal to (in amplitude terms) pulsation value (N minus 1). If the answer to block 202 (D1) is yes, then pulsation value (N) is further evaluated at decision block 204 (D2). If the answer to block 202 (D1) is no, then pulsation value (N) is labeled as a first count by program counter 206 (T1), and the program exits to Adjust Task Delays 100 until a subsequent pulsation value is monitored by microprocessor 31 as pulsation value (N+1).

The effect of labeling pulsation (N) as a first count if the answer to decision block 202 (D1) is no, is to "tell" the microprocessor that the pulsation data stream is not diverging from the baseline data stream. Thus, the microprocessor "knows" that a waveform such as that depicted in FIG. 6, is not beginning to be formed.

Next, returning to the yes response to decision block 202 (D1), decision block 204 (D2) asks whether pulsation value (N) is greater than the baseline data level amplitude (graphically shown at 54 of FIG. 6). If the answer to decision block 204 (D2) is yes, then pulsation value gradient (N) is calculated at task block 208 (T2) by subtracting the immediately prior occurring pulsation value (N−1) from pulsation value (N). If the answer to decision block 204 (D2) is no, the program repeats the steps that were followed when there was a negative answer to decision block 202 (D1), i.e. sample (N) is labeled as a first count by program counter 206 (T1) and the program exits to Adjust Task Delays 100 so the microprocessor can continue "looking" for pulsation divergence.

Once task block 208 (T2) calculates pulsation value gradient (N), decision block 210 (D3) asks whether gradient (N) is greater than a minimum gradient The minimum gradient is equal to the pulsation value gradient (N minus 1). Reference is made to FIG. 6 where lines 66c-66g depict the minimum gradients for corresponding, subsequently depicted pressure pulsation signals 52c-52g. For example, minimum gradient 66c is the minimum gradient for pulsation value 52c.

Returning to the decisional steps in Waveform Beginning Program 200, if the answer to decision block 210 (D3) is yes, then the program proceeds to decision block 212 (D4). If the answer to block 210 (D3) is no, then the program is again exited as it was for a negative answer to the question asked at decision blocks 202 (D1), 204 (D2).

Proceeding from block 210 (D3), decision block 212 (D4) asks whether the program count equals the first count. If the answer to decision block 212 (D4) is no, then the program skips task block 214 (T3) and proceeds to task block 216 (T4) where the program count is increased by one increment. If the answer to decision block 212 (D4) is yes, then task block 214 (T3) initializes the immediately, prior-occurring pulsation value (N−1) as the waveform base.

Initializing a pulsation value as the waveform base is necessary in order for program 200 to "tell" the microprocessor "where" a presently forming pulsation wave began. In other words, once the microprocessor verifies that a pulsation data divergence-convergence wave is beginning to occur, the microprocessor needs to have a reference point approximating the beginning of the pulsation wave. Reference back to FIG. 6 shows that pulsation value 52a is the waveform base of waveform 56. As will soon become apparent, a waveform base value is needed in order for the microprocessor to integrate verified pulsation values because, in order to integrate a pulsation value, the microprocessor needs to have a reference point to integrate from. It is the waveform base that provides such a reference point.

Further referring to FIG. 7B, task block 214 (T3) starts an integrator counter at (N−1). The purpose of this integrator counter will be later described in the discussion of the Waveform Top Program in FIG. 7D.

Next, the Waveform Beginning Program proceeds to task block 216 (T4) which is the same task block that the program proceeded to if the answer to decision block 212 (D4) was negative. Thus, task block 216 (T4) advances the program count by one increment and the program advances to block 218 (T5) where waveform integration is performed on the waveform up to pulsation value (N). This waveform integration is equal to the waveform integral from the waveform area base value initialized in task block 214 (T3) to pulsation value (N).

Next, decision block 220 (D5) asks whether the program counter has reached a preset program count constant. If the answer to block 220 (D5) is yes, then the program proceeds to task block 222 (T6) where the program is labeled to direct the microprocessor to go to Waveform Leading Edge Program 224 and the program count is reset to 0. As described earlier, the program count constant is a way for program 200 to be preset to direct the microprocessor automatically to go to a next program after a specific number of pulsation values have been processed. According to the present practice of the invention, the program count constant is equal to 4.

Finally, continuing from task block 222 (T6), the program proceeds to Adjust Task Delays 100 so that the program exits to Kernel 108 where microprocessor 31 will leave Waveform Beginning Program 200 and go to Waveform Leading Edge Program 224 if block 220 is yes.

Referring back to decision block 220 (D5), if the answer is no, then the program proceeds around task block 222 (T6) and exits to Adjust Task Delays 100 until a next pressure pulsation signal (N+1) is processed by microprocessor 31. Then, Waveform Beginning Program 200 would repeat the above process for pressure pulsation signal (N+1).

The following table is a reference for the immediately-following description of FIG. 7C:

TABLE III

| FIG. C | |
|---|---|
| D1 | Is Pulsation Value (N) < Overflow Constant? |
| D2 | Is Gradient (N) ≧ Minimum Gradient? |
| D3 | Is Program Count Constant Met? |
| T1 | Calculate Pulsation Gradient (N) |
| T2 | Go to Waveform Beginning Program; Set Program Count = 0 |
| T3 | Set Program Count = 0 |
| T4 | Go to Waveform Top Program; Set Program Count = 0 |
| T5 | Advance Program Count by One Increment |
| T6 | Perform Waveform Integration |

Referring now to FIG. 7C, Waveform Leading Edge Program 224 is shown in a flow diagram. In order to picture the pulsation data that Program 224 directs the microprocessor to process, refer to FIG. 6, noting pulsation value data 52c-52g. Program 224 directs the microprocessor to verify that pulsation data is blood-pressure induced and to integrate verified pulsation data during the above-mentioned second phase of pulsation data divergence from baseline counterpressure data.

First, decision block 226 (D1) asks whether pulsation value (N) is less than an overflow constant which is a maximum value that is preset relative to the dynamic range of analog-to-digital converter 30. The practice of the present invention is to set the overflow constant at 95 percent of the maximum dynamic range of converter 30. If the answer to decision block 226 (D1) is yes, task block 228 (T1) calculates a gradient for value (N) by subtracting the immediately prior occurring blood pressure value (N−1) from value (N). If the answer to decision block 226 (D1) is no, then task block 230 (T2) labels the program to direct the microprocessor to go to Waveform Beginning Program 200, and sets the program count to 0. Further, the program then goes to Adjust Task Delays 100 from task block 230 (T2) so that microprocessor 31 can go to Waveform Beginning Program 200 when a next pressure pulsation signal is processed.

Returning to the flow diagram, immediately after task block 228 (T1), decision block 232 (D2) asks whether gradient (N) is greater than or equal to the immediately previous gradient (N−1). If the answer is yes, task block 234 (T3) initializes the Waveform Top Count. Like the previously described program counts, block 224 advances the Program Count for every successively processed pulsation gradient. This enables the program to direct the microprocessor automatically to a next program when a Program Count Constant, to be described, has been met.

If the answer to decision block 232 (D2) is no, then decision block 236 (D3) asks whether a preset Program Count Constant has been met. If the answer to decision block 236 (D3) is yes, task block 238 (T4) labels the program to go to the Waveform Top Program of FIG.

7D, and sets the program count to 0. The program then exits Waveform Leading Edge Program 224, and goes to Adjust Task Delays 100 where, as previously described, it will exit to Kernel 108 so that microprocessor 31 can go to the Waveform Top Program according to the direction of task block 238 (T4).

However, if the answer to decision block 236 (D3) is no, i.e. that the Program Count Constant has not been met, task block 240 (T5) increments the Program Count by 1.

Next, integrator task block 242 (T6) integrates the waveform up to value (N) according to the formula: waveform area (N)=waveform area (N−1)+value (N)−waveform area base value.

Next, the program exits to Adjust Task Delays 100, as previously described, and then exits from Adjust Task Delays 100 to Kernel 108 where microprocessor 31 is directed to Waveform Leading Edge Program 224 or to Waveform Top Program 244.

The following table is a reference for the immediately-following description of FIG. 7D:

TABLE IV

| FIG. 7D | |
|---|---|
| D1 | Is Pulsation Value (N) < Overflow Constant? |
| D2 | Is Gradient (N) ≧ Minimum Gradient? |
| D3 | Is Gradient (N) ≧ 0? |
| D4 | Is Program Count = Waveform Top Constant? |
| D5 | Is Integrator Count > Minimum Integration Count |
| D6 | Is Integrator Count < Maximum Integration Count |
| T1 | Calculate Pulsation Gradient (N) |
| T2 | Go to Waveform Beginning Program; Set Program Count = 0 |
| T3 | Set Program Count = 0 |
| T4 | Perform Waveform Integration |
| T5 | Set Integrator Count = (Integrator Count − N) |
| T6 | Go to Second Artifact Rejection Technique Program; Set Program Count = 0 |
| T7 | Advance Program Count by One Increment |

Referring now to FIG. 7D, Waveform Top Program 244 is shown which directs the microprocessor to process pressure pulsation data during its third phase of divergence from baseline counterpressure data. In order to understand the section of a waveform that is evaluated by Waveform Top Program 244, reference is made back to FIG. 6. In FIG. 6, pulsation data values 52h, 58 and 59 represent pulsation data that occur during the third phase. Thus, the third phase includes pulsation data corresponding to the leading edge of waveform 56 above point of inflection 60 to the point of maximum divergence 58 from baseline 54, and finally to pulsation data 59, converging toward baseline 54.

Decision block 246 (D1) is the first step of Waveform Top Program 244. Like decision block 226 (D1) of Waveform Leading Edge Program 224, decision block 246 (D1) asks whether pulsation value (N) is less than a preset overflow constant which corresponds to a maximum value of the dynamic range of analog-to-digital converter 30. If the answer to block 246 (D1) is yes, task block 248 (T1) calculates pulsation value gradient (N) by subtracting pulsation value (N−1) from pulsation value (N). If the answer to block 246 (D1) is no, task block 250 (T2) labels the program for a Waveform Beginning Program 200, and sets the program count to 0. Then, the program exits to Adjust Task Delays 100, and then to Kernel 108 where microprocessor 31 goes to Waveform Beginning Program 200 to evaluate subsequent pulsation value data.

Returning to pulsation value gradient (N) as calculated by task block 248 (T1), decision block 252 (D2) asks whether pulsation value gradient (N) is greater than or equal to pulsation value gradient (N−1). If the answer to block 252 (D2) is yes, block 250 (T2) labels the program for Waveform Beginning Program 200, sets the program count to 0, and the program exits to Adjust Task Delays 100. Waveform Top Program 244 is exited at this point because, as previously described in FIG. 6, recurring pulsation data values at the top portion of a waveform do not have corresponding gradient values that are greater than or equal to the gradient value for a previous pulsation data value.

Referring back to FIG. 6, this occurs because the data values evaluated by Waveform Top Program 244 occurs after point of inflection 60 of waveform 56, and rounding out at the top of waveform 56.

Returning to FIG. 7D, if the answer to block 252 (D2) is no, decision block 254 (D3) asks whether the pulsation value gradient (N) is greater than or equal to 0. With a yes answer, task block 256 (T3) sets the program count at 0, and integrator task block 258 (T4) calculates the waveform area as equal to waveform area (N−1)+value (N)−waveform base. Program 244 is programmed in this way if the answer to decision block 254 (D3) is yes because a presently-being-processed waveform has not reached its maximum point of divergence from the baseline counterpressure level if the gradients between successively processed pulsation values are still increasing.

Returning to decision block 254 (D3), if the answer is no, Program 244 knows that pulsation value (N) indicates that the waveform is beginning to converge toward the baseline level, because the gradients between successively processed pulsation values are decreasing. This corresponds to the downwardly sloping side 62b of waveform 56 in FIG. 6.

Next, returning to FIG. 7D along the "no" response to decision block 254 (D3), decision block 260 (D4) asks whether the program count equals the waveform top count constant. The waveform top count constant is a preset constant that, when met, directs the microprocessor, through Program 244, to determine if processing of a presently-being-processed waveform should be completed. If the count constant is met, then the program directs the microprocessor to calculate a final waveform integral for the waveform. The current practice of the present invention is to set the Waveform Top Count Constant at 4. Thus, after Program 244 directs the microprocessor to process four successive pulsation values with corresponding negative gradients, during the third phase of divergence-convergence, the microprocessor is directed to calculate a waveform integral according to the program steps next to be described.

It is important to note that, during this third phase, the present method of practicing the invention is to stop processing pulsation values after the fourth pulsation value having a corresponding negative gradient because pulsation values occurring after these four values are often not blood-pressure induced. Further, processing such pulsation data (which, referring to FIG. 6, graphically corresponds to the remainder of downwardly-sloping side 62b of waveform 56) is also time-consuming. Increased time is undesirable because the longer the blood pressure measurement period, the more discomfort for the patient.

Returning to FIG. 7D, if the answer to decision block 260 (D4) is yes, then task block 262 (T5) sets the integration count at [integration count−N] so that decision blocks 264 (D5), 266 (D6) can evaluate the integration count relative to a minimum integration count and maximum integration count. These integration, or program, counts provide yet another artifact check by "telling" the microprocessor if a present, completely processed waveform has occurred in a number of counts (reflecting a "waveform width") corresponding to a real time period indicative of a blood pressure induced waveform and not an artifact. Thus, the maximum and minimum integration counts provide a "waveform width window" against which a presently calculated waveform's width (i.e., the waveform's total integration counts) can be compared for acceptance purposes.

Further, these maximum and minimum counts are repeatedly adjusted values that are adjusted differently relative to whether a present waveform is accepted because it is within the "window", or rejected because it is outside the "window". The specific "window" adjustments will be described shortly, however, at this point, the adjustments will be described generally to provide an understanding of why the adjustments are made.

The program that directs the microprocessor to make the yet-to-be described adjustments is not depicted in FIG. 7D. However, the following description of these adjustments will allow those skilled in the art to use the invention.

When a present waveform is accepted, two types of "window" adjustments are made. The first type of adjustment is to increase the maximum count and decrease the minimum count by an identical, preset value. Thus, the "window" is enlarged by a preset amount every time a subsequent waveform's width is accepted, i.e., is within its corresponding "waveform width window" criteria. This enlargement is based on our finding that, during a measurement cycle, as the blood pressure impulse is increasing to a maximum, the width of recurrently monitored waveforms increases.

The second type of adjustment is to adapt the aforementioned "window enlarging" based on the relationship of a presently monitored waveform's width to an immediately, previously monitored waveform's width. As will be described, the above "window enlarging" is skewed slightly to the window's maximum-count "side" when a present waveform's width is greater than a previous waveform's width by enlarging the window's maximum-count "side" more than its minimum-count "side". When a present waveform's width is less than a previous waveform's width, the "window enlarging" is skewed slightly to the window's minimum-count "side" by enlarging the window's minimum-count "side" more than its maximum-count "side".

If the present waveform's width is equal to the previous waveform's width, then this second type of adjustment is not made.

When a present waveform is rejected, one type of "window" adjustment is made relative to whether the waveform's width was outside of the "window's" minimum-count side or the "window's" maximum-count side The specific "window" adjustments that are made when a present waveform is rejected will be described shortly.

Before describing the specific "window" adjustments, it is important to note how the programs depicted in FIGS. 7B-7D direct the microprocessor to "track" a waveform's width by keeping an integration count corresponding to the number of pulsation values that have been integrated during the three phases of pulsation divergence-convergence from baseline data. The microprocessor is directed to keep this integration count according to task block 114 of program 100 of FIG. 7B.

Referring back to FIG. 7B, task block 114 directs the microprocessor to begin an integration count once the microprocessor verifies that a first pulsation value is diverging from baseline data. Generally, yes responses to blocks 102 (T1), 106 (T2), 110, 112 of program 100 direct the microprocessor to the point where just such a first pulsation value has diverged from baseline data. Finally, it is important to remember that this pulsation value divergence-convergence from baseline data occurs in repeating series of the aforementioned three phases, wherein any one series of divergence-convergence is represented by the waveform of FIG. 6 with associated pulsation data.

Returning to FIG. 7D, the part of the program that uses the minimum and maximum count criteria to check "waveform width" will now be discussed. Decision block 264 (D5) asks whether the integration count is greater than a minimum integration count. If the answer to decision block 264 (D5) is yes, decision block 266 (D6) asks whether the integration count is less than a maximum integration count. If the answer is also yes to decision block 266 (D6), then task block 268 (T6) labels the program for the program of FIG. 9 and sets the program count to 0. The program exits to Kernel 108 so that microprocessor 31 can go to the waveform-specific area data evaluator program of FIG. 9.

Concerning the aforementioned "window" adjustments, it is important to note that no "window" adjustments are performed relative to the first waveform integral that is processed at the first pulsation-containing cuff counterpressure level because there is no previous waveform's width against which to compare. Rather, this first waveform's width is checked against preset, experimentally-established minimum and maximum integration counts. If the first waveform's width is within the preset criteria, then the waveform's integral is stored and the measurement cycle continues. If the first waveform's width is outside the preset criteria, then the waveform's integral is rejected and the measurement cycle continues until a first waveform's width is accepted. Presently, the method of practicing the invention is to use 20 for the minimum count and 36 for the maximum count.

The following process is used to adjust an established "waveform width window" based on the relationship of a presently monitored waveform's width to a previously monitored waveform's width. This process is followed for each waveform after a first waveform is accepted.

For a present "window", the minimum and maximum integration counts are adjusted based on the relationship of a present, accepted waveform's width (total integration count) and the immediately, previously-developed waveform's width (total integration count). There are three possibilities concerning this relationship.

First, if the present waveform's width is equal to the previous waveform's width, then the integration count criteria are adjusted by adding seven to the maximum count and subtracting seven from the minimum count (i.e., the aforementioned first type of adjustment). Second, if the present waveform's width is greater than the previous waveform's width then the maximum integration count equals the present waveform's width plus 9 and the minimum integration count equals the present waveform's width minus 7 (i.e., the aforementioned first and second types of adjustment). Third, if the present waveform's width is less than the previous waveform's width, then the minimum integration count equals the present waveform's width minus 9, and the maximum integration count equals present waveform's width plus 7 (i.e., the aforementioned first and second types of adjustment).

Thus, the preferred practice of the present invention is to adjust the "window" criteria more toward the maximum or minimum count based on the relationship of a presently-accepted waveform's integration count to a previously monitored waveform's integration count. If the present waveform's integration count is greater than the previous waveform's integration count, then the overall waveform width window criteria is adjusted more with respect to the maximum count (longer real time period of waveform) than the minimum count. If the present waveform's integration count is less than the previous waveform's integration count, then the overall width window as represented by the minimum and maximum integration counts of FIG. 7D, is adjusted more with respect to the minimum count (shorter real time period of waveform) than the maximum count.

Finally, if a present waveform is rejected because its integration count is outside the waveform width window criteria as represented by the minimum and maximum integration counts, the integration counts are adjusted relative to whether the present waveform-integration count was greater than the maximum count, or less than the minimum count. If the present waveform's count is less than the minimum count, then the minimum integration count is decreased by two. If the present waveform's count is greater than the maximum count, then the maximum integration count is increased by two.

Referring back to block 264 (D5) and block 266 (D6), if the answer is no to either of these blocks, Waveform Top Program 244 directs the microprocessor to reject the entire waveform area data value as artifact because the waveform occurred over a real time period that has been experimentally shown to be too short or too long to be indicative of a blood-pressure induced waveform.

Further, task block 250 (T2) labels the program for Waveform Beginning Program 200, sets the program count at 0, and the program exits to Adjust Task Delays 100. Then, the program exits to Kernel 108 so that microprocessor 31 can repeat the programs employing first artifact rejection technique 32 for recurring pulsation data exhibiting the three phases of divergence.

Finally, referring back to decision block 260 (D4), if the program count is not equal to the waveform top count constant, then the program count is increased one increment by task block 270 (T7). Thus, the microprocessor knows that there have been less than four pulsation values having negative gradients. Next, integrator task block 258 (T4) integrates the waveform according to the formula: waveform integral+pulsation value (N)—waveform area base. Then, the program exits to Adjust Task Delays 100 so that microprocessor 31 can repeat Program 244 for a recurring pulsation data value.

Figure 8A:
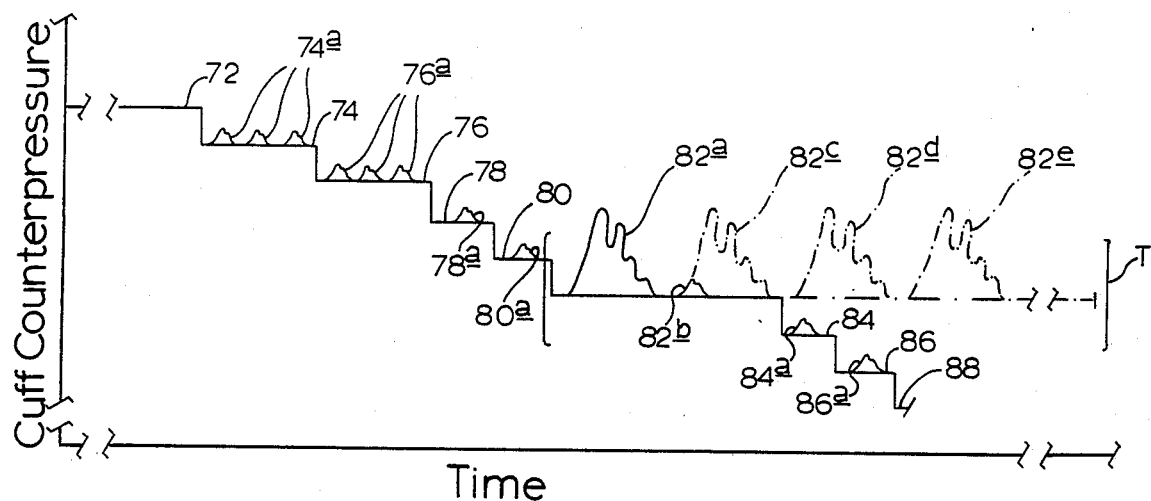
FIG. 8A is a fragmented graph of cuff counterpressure decreasing over time, showing a series of cuff counterpressure levels wherein the waveforms depicted are monitored by the method of the present invention.

Turning now to FIG. 8A, stepped, decreasing cuff counterpressure levels and associated pressure waveforms are shown in order to depict graphically what has previously been described as first waveform area data evaluator 36 and second artifact rejection technique 42. It is important to note that the description of FIG. 8A, as well as FIGS. 8B–8D, 9, depict how the microprocessor processes waveform integrals that have been developed by the microprocessor under the direction of the programs depicted in FIGS. 7A–7D.

Thus, each waveform depicted in FIG. 8A represents pulsation data that has been processed by the microprocessor, seriatim, in order to verify that the data is blood pressure-induced, and to integrate verified data as the data exhibits one of the three aforementioned phases of divergence from baseline counterpressure data.

Finally, after the microprocessor receives pulsation data relative to a point to the right of each waveform's peak, thus at a point where pulsation data is converging to baseline data, the microprocessor stores the integral of each waveform, which is calculated from the previously described waveform base to the waveform processing ending point. Then, waveform integrals for each waveform that the microprocessor verifies and integrates by the aforementioned technique 32 and integrator 34 are further processed to determine one waveform-specific area data value for each counterpressure level.

This further processing of waveform integrals, each representing a series of the aforementioned three phases of pulsation divergence from baseline data, will be described in the discussion of FIGS. 8A–8D, 9. Referring back to the block diagram of FIG. 5, it is important to note that the remainder of the description of the invention concerns how the microprocessor is directed by what has previously been described as first waveform area data evaluator 36 to determine a waveform-specific area data value for the first two counterpressure levels at which pulsation divergence occurs.

Further, after the microprocessor determines an area data value for the first two counterpressure levels, the second artifact rejection technique program directs the microprocessor to generate a prediction curve from the two area data values. This prediction curve directs the microprocessor to use a different technique for determining an area data value for the third and subsequent counterpressure levels than the technique of evaluator 36 that was applied to the first two counterpressure levels.

As one final overview point, a significant difference in the two different techniques that the microprocessor uses to determine an area data value for the first two counterpressure levels, and then for the remaining counterpressure levels, is that three pulsation waveforms must be processed at each of the first two levels, whereas generally only one waveform need be processed at the third and subsequent levels.

Referring now to FIG. 8A, as the counterpressure is progressively reduced from a point above systolic pressure to the ending counterpressure, pressure waveforms will occur as discussed in FIG. 6. FIG. 8A depicts no pressure waveforms at a counterpressure level 72 because counterpressure level 72 is above systolic pressure. Then, beginning with a counterpressure level 74, verified-to-be-blood-pressure induced waveforms 74a, 74b, 74c are processed by microprocessor 31 (i.e. waveform integrals are developed under the direction of programs 100, 124, 144).

Next, the microprocessor directs valve 22 to decrease counterpressure to a next counterpressure level 76, where the microprocessor processes verified-to-be-blood-pressure induced waveforms 76a, 76b, 76c and develops corresponding waveform integrals.

At each level 74, 76, after the microprocessor develops three waveform integrals for the three waveforms and before counterpressure is decreased, a computer program directs microprocessor 31 to evaluate the three waveform integrals in order to calculate one waveform-specific area data value for each counterpressure level 74, 76.

Figure 9:
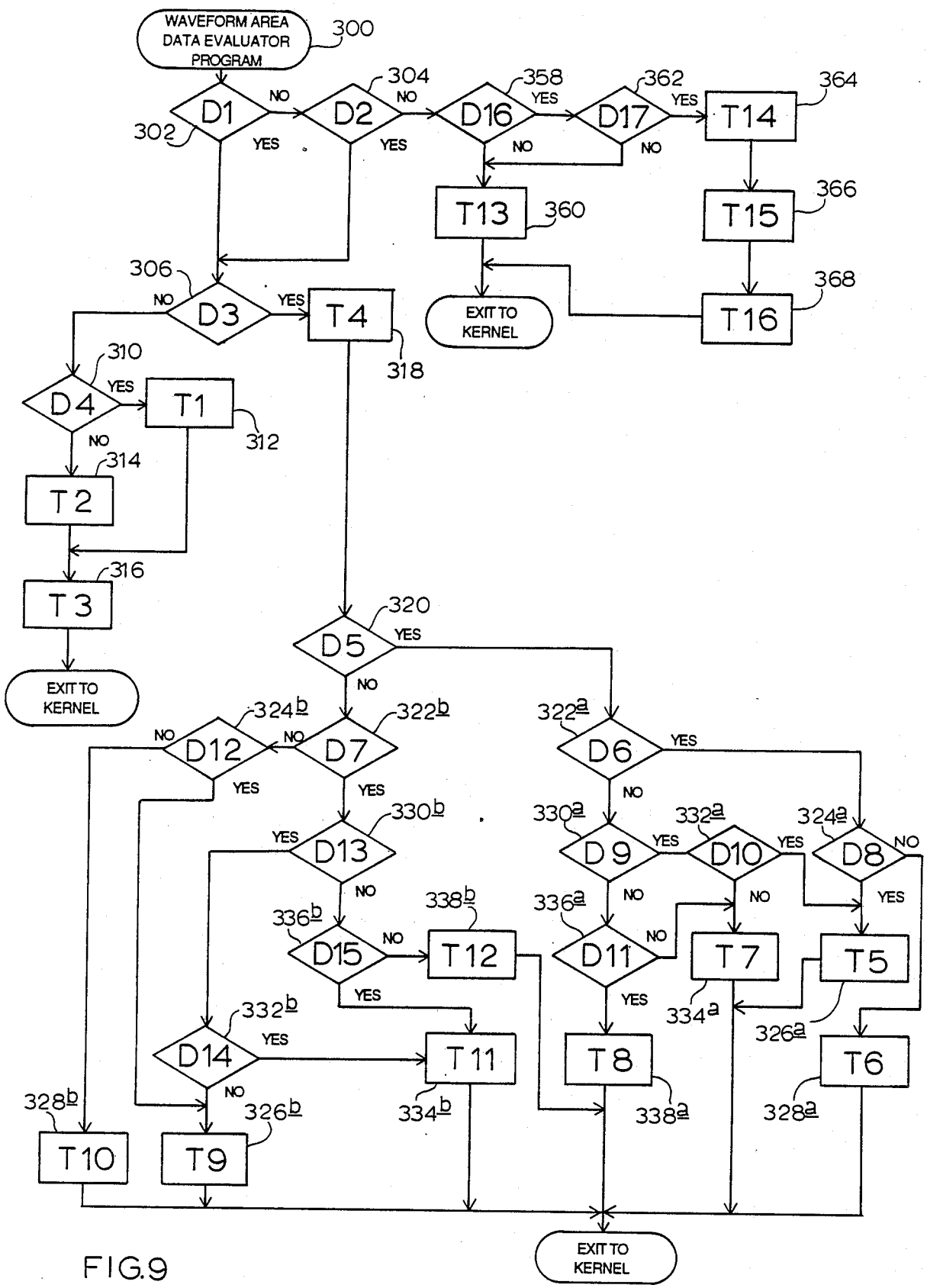
FIG. 9 is a computer-program flow chart further illustrating computer-based implementation of the invention.

Next, the calculation used by the microprocessor to determine one area data value from three waveform integrals at either counterpressure levels 74, 76 will be described. Generally, to perform the calculation, the microprocessor chooses the two waveform integrals that are closest to each other, averages the two integrals, and stores a final averaged waveform-specific area data value. The program which directs microprocessor 31 is depicted in FIG. 9. Turning now to FIG. 9, in order to determine one waveform-specific area data value for cuff counterpressure level 74, 76, the microprocessor is directed by a portion of Second Artifact Rejection Technique 300. This portion has been previously depicted and described as first waveform area data evaluator 36. The following table is a reference for the immediately following description of FIG. 9, and for the subsequent description of FIG. 9:

TABLE V

FIG. 9

| | |
|---|---|
| D1 | Is the Microprocessor Monitoring First Cuff Counterpressure Level? |
| D2 | Is the Microprocessor Monitoring Second Cuff Counterpressure Level? |
| D3 | Has the Microprocessor Developed 2 Waveform Integrals? |
| D4 | Is Sample (N) = 1st Waveform Integral |
| D5 | Is WF1 > WF2? |
| D6 | Is WF2 > WF3? |
| D7 | Is WF2 > WF3? |
| D8 | Is (WF1 − WF2) > (WF2 − WF3)? |
| D9 | Is WF1 > WF3? |
| D10 | Is (WF1 − WF3) > (WF3 − WF2)? |
| D11 | Is (WF3 − WF1) > (WF1 − WF2)? |
| D12 | Is (WF3 − WF2) > (WF2 − WF1)? |
| D13 | Is WF1 > WF3? |
| D14 | Is (WF2 − WF1) > (WF1 − WF3)? |
| D15 | Is (WF2 − WF3) > (WF3 − WF1)? |
| D16 | Is Sample (N) ≦ Upper Bound of Predicted Value |
| D17 | Is Sample (N) ≧ Lower Bound of Predicted Value |
| T1 | Initialize Waveform Integral (N) as WF1 |
| T2 | Initialize Waveform Integral (N) as WF2 |
| T3 | Go to Waveform Beginning Program; Set Program Count = 0 |
| T4 | Initialize Waveform Integral (N) as WF3 |
| T5 | Average WF2 and WF3 = (WF2 + WF3)/2 |
| T6 | Average WF1 and WF2 = (WF1 + WF2)/2 |
| T7 | Average WF1 and WF3 = (WF1 + WF3)/2 |
| T8 | Average WF1 and WF2 = (WF1 + WF2)/2 |
| T9 | Average WF1 and WF2 = (WF1 + WF2)/2 |
| T10 | Average WF2 and WF3 = (WF2 + WF3)/2 |
| T11 | Average WF1 and WF3 = WF1 + WF3)/2 |
| T12 | Average WF3 and WF2 = (WF3 + WF2)/2 |
| T13 | Go to Waveform Beginning Program; Set Program Count = 0 |
| T14 | Store Waveform Integral (N) |
| T15 | Store Baseline Counterpressure (N) |
| T16 | Decrease to next Baseline Counterpressure |

Referring now to FIG. 9, Program 300 begins with decision block 302 (D1) which asks whether the apparatus is at the first cuff counterpressure level at which pulsation values were processed by microprocessor 31. If the answer to decision block 302 (D1) is no, decision block 304 (D2) asks whether the apparatus is at the second cuff counterpressure level at which pulsation values were monitored by microprocessor 31.

Thus, decision blocks 302 (D1) and 304 (D2) direct the microprocessor to determine whether the apparatus is at counterpressure levels such as level 74, 76 depicted in FIG. 9A. If the answer is yes to either decision block 302 (D1) or 304 (D2), then Program 300 directs the microprocessor to evaluate waveform-specific integrals that have been developed at the corresponding first or second cuff counterpressure levels according to what has been previously depicted and described in FIG. 5 as first waveform area data evaluator 36.

Before describing the remainder of FIG. 9, it is important to note that a negative response to decision blocks 302 (D1) and 304 (D2) directs the microprocessor to continue to the portion of the program beginning with decision block 358 (D16). This portion of FIG. 9 describes how Program 300 evaluates waveform integrals that have been developed from pulsation data processed by the microprocessor at counterpressure levels below the first two cuff counterpressure levels. This portion of FIG. 9 will be described after the discussion of FIG. 8B which depicts the generation of what has been previously called a prediction curve, and shows how the microprocessor is directed to use technique 42 to predict an area data value for a next counterpressure level.

Returning back to the yes response to either decision blocks 302 (D1) or 304 (D2) of FIG. 9, decision block 306 (D3) asks whether two waveform integrals have been developed by the microprocessor for the present counterpressure level (e.g. levels 74, 76 of FIG. 8A). If the answer to decision block 306 (D3) is yes, then the present waveform integral is a third integral and Program 300 directs the microprocessor to chose the closest two of the three waveform integrals, average the closest two waveform-specific area data values, and calculate one, averaged waveform-specific area data value for the counterpressure level. The steps of this process begin with task block 318 (T4) and will be described soon. However, the steps that Program 300 follows if the answer to decision block 306 (D3) is no will be described first.

If the answer to decision block 306 (D3) is no, then decision block 310 (D4) asks whether the present waveform integral is the first waveform integral developed by the microprocessor for the present counterpressure level. If the answer to decision block 310 (D4) is yes, then task block 312 (T1) initializes the current waveform-specific area data value as WF1. If the answer to decision block 310 (D4) is no, then the present waveform integral is the second integral and task block 314 (T2) initializes the present waveform integral as WF2.

Next, once the present waveform integral has been initialized by the microprocessor, task block 316 (T3) labels the program for Waveform Beginning Program 200 and the program exits to Kernel 108 so that microprocessor 31 can go to Waveform Beginning Program 200 and develop a next integral for a next processed waveform.

Returning back to the flow diagram, when there is a yes response to decision block 306 (D3), task block 318 (T4) initializes the present waveform integral as WF3. The remainder of FIG. 9 shows the steps that Program 300 follows in order to chose the closest two of the three integrals of the present counterpressure level (i.e., levels 74, 76 of FIG. 8A).

Moving from task block 318 (T4) decision block 320 (D5) asks whether WF1 is greater than WF2. If the answer to decision block 320 (D5) is yes, then decision block 322a (D6) asks whether WF2 is greater than WF3. If the answer to decision block 320 (D5) is no, then decision block 322b (D7) asks whether WF2 is greater than WF3.

As shown in FIG. 9, once Program 300 reaches decision blocks 322a (D6) or 322b (D7), the remaining steps after decision blocks 322a (D6) or 322b (D7) will follow one of twelve paths based on the relative values for WF1, WF2, WF3. First, the six alternate paths that are possible after decision block 322a (D6) will be discussed. Then, the six paths that are possible after decision block 322b (D7) will be discussed.

If the answer to decision block 322a (D6) is yes, then decision block 324a (D8) asks whether (WF1−WF2) is greater than (WF2−WF3). Continuing on with the flow diagram after block 324a before returning to the possibility of a negative answer to decision block 322a (D6), a yes or a no answer to decision block 324a (D8) allows Program 300 to decide which two of WF1, WF2, WF3 are the closest to each other. If the answer to decision block 324a is yes, then WF2 and WF3 are the two closest area data values, and task block 326a (T5) averages WF2 and WF3 in order to calculate one waveform-specific area data value for the current cuff counterpressure level. If the answer to decision block 324a (D8) is no, then WF1 and WF2 are the two closest area data values and task block 328a (T6) calculates an average waveform-specific area data value for the current cuff counterpressure level.

Returning now to the possibility of a negative answer to decision block 322, decision block 330a (D9) asks whether WF1 is greater than WF3. If the answer to decision block 330a (D9) is yes, then decision block 332a (D10) asks whether (WF1−WF3) is greater than (WF3−WF2).

Again the description will continue with steps following decision block 332a (D10) before describing the possibility of a negative answer to decision block 330a (D9). If the answer to decision block 332a (D10) is yes, then WF2 and WF3 are the two closest area data values and task block 326a (T5) would calculate an average waveform-specific area data value for the current cuff counterpressure level. If the answer to decision block 332a (D10) is no, then WF1 and WF3 are the closest area data values and task block 334a (T7) would calculate an average waveform-specific area data value from WF1 and WF3.

Returning now to the possibility of a negative answer to decision block 330a (D9), decision block 336a (D11) asks whether (WF3−WF1) is greater than (WF1−WF2). If the answer to decision block 336a (D11) is yes, then WF1 and WF2 are the two closest area data values and task block 338a (T8) calculates an average waveform-specific area data value from WF1 and WF2. If the answer to decision block 336a (D11) is no, then WF1 and WF3 are the two closest area data values and task block 334a (T7) would calculate an average waveform-specific area data value from WF1 and WF3.

Returning to the possibility of a negative answer to decision block 320 (D5), decision block 322b (D7) asks whether WF2 is greater than WF3. If the answer to decision block 322b (D7) is no, then decision, block 324b (D12) asks whether (WF3−WF2) is greater than (WF2−WF1). If the answer to decision block 324b (D12) is yes, then WF1 and WF2 are two closest area data values and task block 326b (T9) calculates and stores an average waveform-specific area data value based on WF1 and WF2. If the answer to decision block 324b (D12) is no, then WF2 and WF3 are the two closest area data values and task block 328b (T10) calculates and stores an average waveform-specific area data value from WF2 and WF3.

Returning now to the possibility of a positive answer to decision block 322b (D7), decision block 330b (D13) asks whether WF1 is greater than WF3. If the answer to decision block 330b (D13) is yes, then decision block 332b (D14) asks whether (WF2−WF1) is greater than (WF1−WF3). Again, the description will continue with the steps after decision block 332 before describing the possibility of a negative answer to decision block 330b (D13). If the answer to decision block 332b (D14) is no, then WF1 and WF2 are the two closest area data values and decision block 326b (T9) calculates and stores an average waveform-specific area data value based on WF1 and WF2. If the answer to decision block 332b (D14) is yes, then WF1 and WF3 are the two closest area data values and task block 334b (T11) calculates and stores an average waveform-specific area data value from WF1 and WF3.

Next, returning to possibility of a negative answer to decision block 330b (D13), decision block 336b (D15) asks whether (WF2−WF3) is greater than (WF3−WF1). If the answer to decision block 336b (D15) is yes, then task block 334b (T11) calculates and stores an average, waveform-specific area data value from WF1 and WF3. If the answer to decision block 336b (D15) is no, then WF3 and WF2 are the two closest area data values and task block 338b (T12) calculates an average, waveform-specific area data value from WF3 and WF2.

Finally, after task blocks 326a (T5), 326b (T9), 328a (T6), 328b (T10), 334a (T7), 334b (T11), 338a (T8), or 338b (T12) calculate and store an average waveform-specific area data value, Program 300 exits to Kernel 108 so that the microprocessor can go to the previously described programs in FIGS. 7B-7D to develop a next waveform integral from pulsation data divergence at a next counterpressure level.

Referring back to FIG. 8A, after the microprocessor determines a waveform-specific area data value for counterpressure levels 74, 76, what has previously been described as second artifact rejection technique 42 directs the microprocessor to generate a prediction curve using the area data values of counterpressure levels 74, 76. This prediction curve, and the corresponding predictive algorithm included in what has previously been described as second artifact rejection technique 42 will be explained later in the description of FIGS. 8B, 8C.

However, to describe generally what happens, at cuff counterpressure level 76, the microprocessor is directed by a program employing second artifact rejection technique 42 to predict an expected-to-be-stored waveform-specific area data value for a pressure waveform that as yet, has not been processed at a next counterpressure level 78. The microprocessor makes this prediction from a prediction curve that the microprocessor generated from the area data values of levels 74, 76.

Referring to FIG. 8A, blood pressure induced waveform 78a represents a waveform that is actually processed by Microprocessor 31 at counterpressure level 78. A waveform integral developed from measured waveform 78a by the microprocessor according to the programs in FIGS. 7A-7D is now evaluated by whether it meets the criterion of the predicted waveform-specific area data value generated by the microprocessor under the direction of second artifact rejection technique 42. The evaluation includes checking whether the waveform integral of waveform 78a is within the upper and lower bounds of the corresponding predicted waveform-specific area data value generated by the microprocessor under the direction of second artifact rejection technique 42.

In order to explain how the microprocessor evaluates the waveform integral of waveform 78a, reference is now made to FIG. 9, and specifically to the portion of the waveform area data evaluator program beginning with decision block 358 (D16). Referring back to the previous discussion of FIG. 9, it is important to note that program 300 does not direct the microprocessor to decision block 358 (D16) unless the answer to decision blocks 302 (D1), 304 (D2) is no. Thus, program 300 only directs the microprocessor to the portion of program 300 beginning with decision block 358 (D16) when the microprocessor is processing data at the third and following counterpressure levels.

The portion of Program 300 which directs the microprocessor's evaluation of waveform integrals developed from pulsation waveforms occurring at the third and subsequent counterpressure levels will be discussed after the description of FIG. 8B because FIG. 8B explains how the microprocessor is directed by second artifact rejection technique 42 to predict an expected-to-be-stored waveform-specific area data value for the third and subsequent counterpressure levels. Because it is first necessary to understand the prediction of area data values using second artifact rejection technique 42, the explanation of how program 300 uses the predicted area data value of technique 42 will be postponed until after the description of technique 42 in FIG. 8B.

Still referring to FIG. 8A, it is sufficient for now to keep in mind that program 300 uses a different method of determining one waveform-specific area data value for counterpressure levels 78-86 than the previously described method of determining one area data value for counterpressure levels 74, 76. Therefore, with the exclusion of counterpressure level 82, the remainder of FIG. 8A depicts how the present invention would continue the measurement cycle if the waveform integral developed by the microprocessor for pressure waveforms at each counterpressure level met the criterion set by the predicted area data value for each corresponding counterpressure level.

Thus, after program 300 determined one area data value for counterpressure level 78 by a portion of the program yet to be described, the microprocessor directs valve 22 to reduce counterpressure to a next counterpressure level 80.

Next, the aforementioned, and yet to be further explained, prediction and determination process would be repeated at counterpressure level 80. The process would repeat for subsequent counterpressure levels provided each waveform integral of each pulsation waveform at each subsequent cuff counterpressure level fell within the bounds of a predicted waveform-specific area data value (predicted by the microprocessor under the direction of second artifact rejection technique 42).

Further, FIG. 8A shows how the present invention responds when a waveform integral of a pulsation waveform occurring at a counterpressure level does not fall within the bounds of a previously predicted area data value. A counterpressure level 82 is shown with five blood pressure induced waveforms 82a-82e depicted thereon. Waveforms 82a, 82b are shown by solid lines in order to show a first scenario. Then, blood pressure induced waveform 82c is depicted by dot-dashed lines to represent a second scenario wherein waveform 82c occurs instead of waveform 82b, and further, wherein waveforms 82d, 82e would also occur at cuff counterpressure level 82.

First, the first scenario in which blood pressure induced waveforms 82a, 82b occur will be described. After microprocessor 31 develops a waveform integral of waveform 82a, Program 300 determines if the waveform integral is within the bounds of its corresponding predicted area data value. Further, FIG. 8A depicts waveform 82a as larger than previously accepted waveforms 78a, 80a in order to graphically represent that the developed waveform integral of waveform 82a is outside the bounds of the corresponding predicted waveform-specific area data value of waveform 82a.

Thus, Program 300 rejects the waveform integral of waveform 82a because the value is outside the bounds of the previously predicted waveform-specific area data value for waveform 82a. In this specific case, because waveform 82a is substantially larger than previously accepted waveforms 78a, 80a, the developed waveform integral of waveform 82a would be rejected by the microprocessor under the direction of Program 300 because it is greater than the upper bounds of the previously predicted waveform-specific area data value for waveform 82a. Again, the way in which Program 300 of FIG. 9 determines whether to accept the waveform integral at the third and subsequent counterpressure levels will be described following the description of FIG. 8B.

However, unlike its depiction in FIG. 8A, it is also possible that waveform 82a could be substantially smaller than previously accepted waveform 78a, 80a. Then, the developed waveform integral for this hypothetical, undepicted waveform 82a would be rejected by the microprocessor because the measured area data value would be outside the lower bounds of the previously predicted waveform-specific area data value for this hypothetical, undepicted waveform 82a.

Next, returning to the point where the microprocessor rejects the waveform integral of waveform 82a, the microprocessor directs valve 22 to stay at counterpressure level 82. Then, microprocessor 31 develops a waveform integral of a next-occurring waveform 82b according to the programs described in FIGS. 7A-7D. Then, the microprocessor determines whether the integral of waveform 82b is within the bounds of its corresponding predicted area data value (remember that microprocessor 31 predicts the area data value according to technique 42 and determines whether to accept the integral of waveform 82b under the direction of yet-to-be-described portion of Program 300).

As depicted in FIG. 8A, waveform 82b is substantially the same size as previously accepted waveforms 78a, 80a. This graphically depicts that the integral of waveform 82b is accepted by the microprocessor because the measured area data value falls within the bounds of the predicted waveform-specific area data value.

Then, upon acceptance of the waveform-specific area data value for waveform 82b by microprocessor 31, the microprocessor directs valve 22 to reduce counterpressure by a next increment. The same process would repeat, including predicting a subsequent, expected-to-be-stored waveform-specific area data value, developing a waveform integral for a next-occurring pressure waveform, and determining whether the waveform integral of the waveform falls within the bounds of the predicted waveform-specific area data value.

Finally, remaining at counterpressure level 82 of FIG. 8A, the second scenario will be described in which waveform 82b does not occur, but rather waveforms 82c, 82d, 82e occur and corresponding waveform integrals are developed by microprocessor 31.

FIG. 8A depicts waveforms 82c, 82d, 82e as also substantially larger than previously accepted waveforms 78a, 80a in order to graphically depict that the corresponding, developed waveform integrals of waveforms 82c, 82d, 82e are outside the bounds of the corresponding predicted area data value for counterpressure level 82. Thus, microprocessor 31 would reject the waveform integrals of waveforms 82c, 82d, 82e because the measured area data values would be outside the bounds of the predicted area data value.

Further, the microprocessor directs valve 22 to stay at counterpressure level 82 and continues to develop waveform integrals for subsequently occurring pulsation waveforms.

Further, FIG. 8A depicts a fragmented portion of counterpressure level 82 by dot-dashed lines in order to show that the aforementioned, developing, predicting, and determining steps carried out by microprocessor 31 under the direction of the corresponding programs would repeat, until either a developed waveform integral of a waveform was accepted by the microprocessor because it was within the bounds of the predicted area data value, or until time period "T" occurred as shown in FIG. 8A.

If time period "T" occurs without the microprocessor having accepted a waveform integral of a subsequently occurring waveform at counterpressure level 82, then the apparatus would abort the entire measuring cycle, and the microprocessor would direct valve 22 to deflate cuff 14. Currently, the preferred practice of the present invention is to use a 30 second time period as time "T".

Figure 8B:
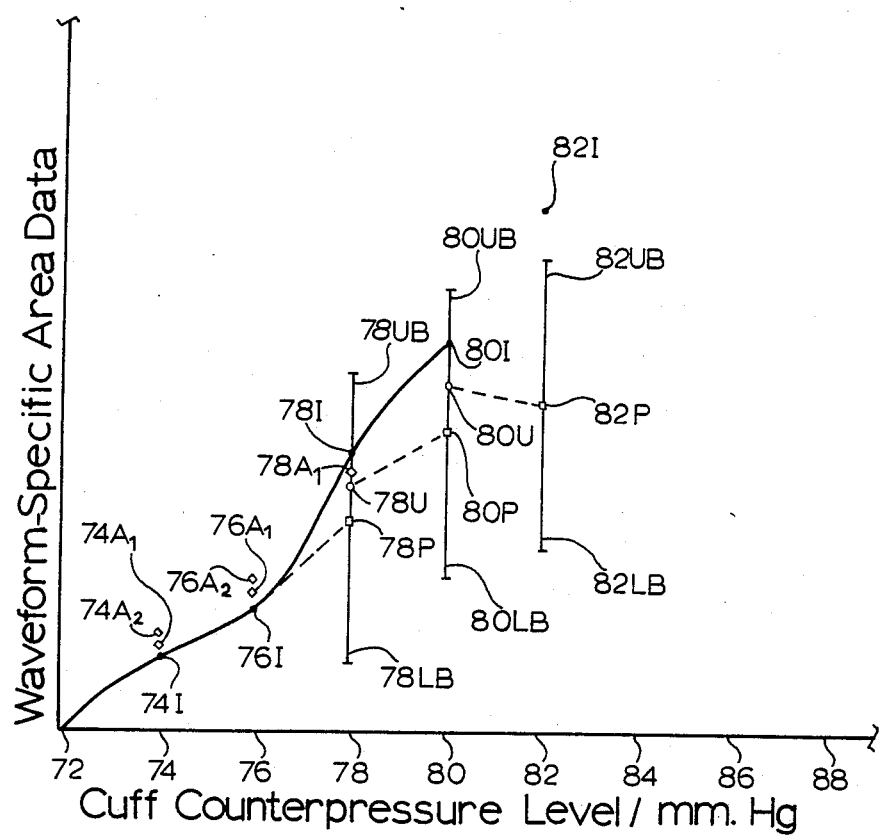
FIG. 8B is a fragmented graph of waveform-specific area data vs. cuff counterpressure levels that depicts how the second artifact rejection technique, mentioned earlier, predicts a subsequent, expected-to-be-stored waveform area-data value for a subsequent cuff counterpressure level.
Figure 8C:
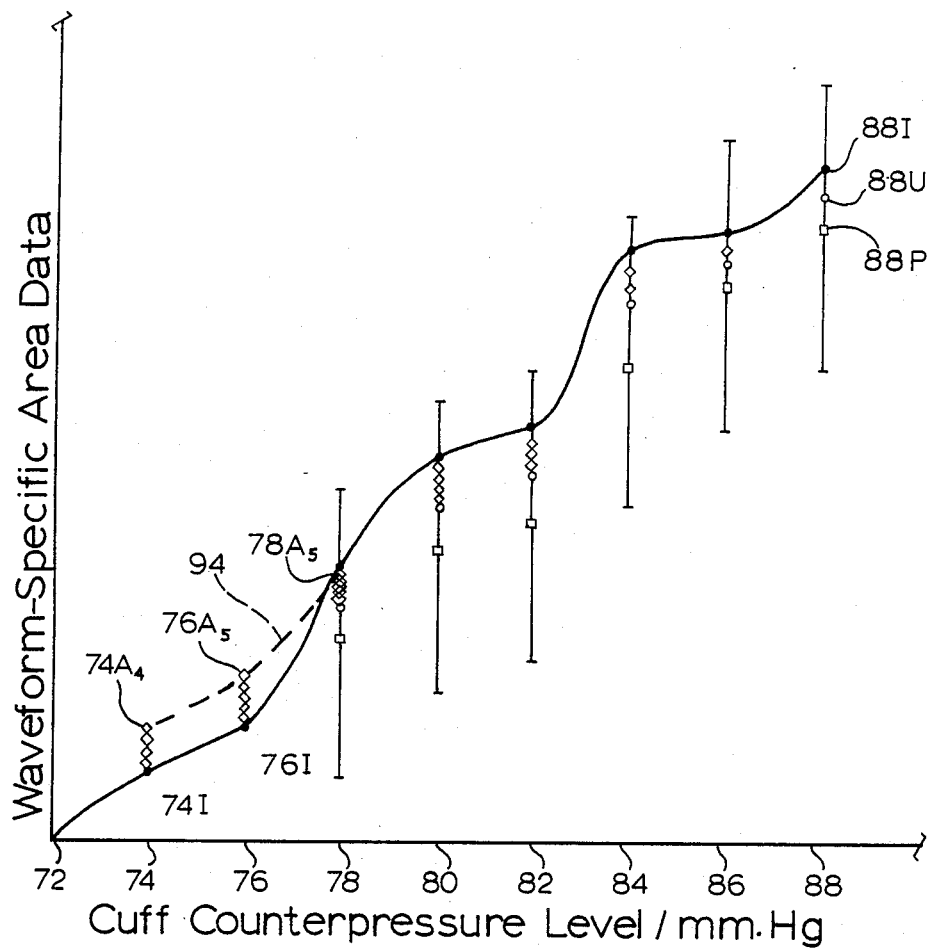
FIG. 8C is a fragmented graph of waveform area data vs. cuff counterpressure levels illustrating the "smoothing" technique referred to earlier.
Figure 8D:
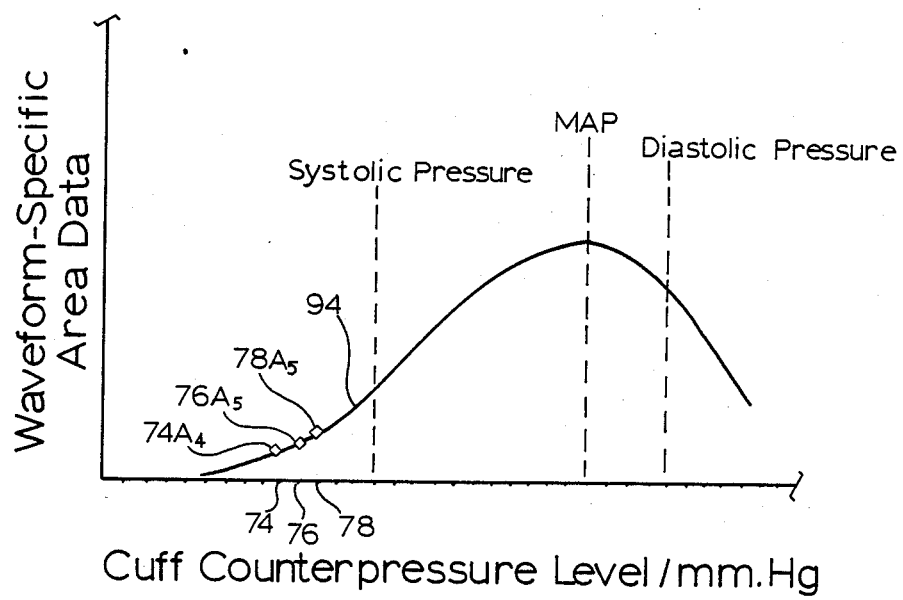
FIG. 8D is a graph of waveform area data vs. cuff counterpressure levels for an entire measuring cycle of a living test subject.

Turning now to FIGS. 8B–8D, three graphs of waveform-specific area data values vs. cuff counterpressure levels are shown. FIGS. 8B and 8C are fragmented graphs wherein the vertical spread of points are exaggerated in order to graphically depict the operation of second artifact rejection technique 42 and data smoother 46.

Turning first to FIG. 8B, cuff counterpressure levels 72–82 are shown wherein solid points 74I–82I correspond to developed waveform integrals for each counterpressure level. Further, referring to FIG. 8B, solid points 74I and 76I also correspond to stored waveform-specific area data values determined by microprocessor 31 for counterpressure levels 74, 76 according to the previously described portion of Program 300 of FIG. 9. There is no corresponding waveform-specific area data value for cuff counterpressure level 72 because, as discussed in FIG. 8A, no blood pressure induced waveform occurred at counterpressure level 72 because it was above systolic pressure.

Referring now to counterpressure level 78 of FIG. 8B, second artifact rejection technique 42 directs the microprocessor to predict a subsequent, expected-to-be-stored waveform-specific area data value 78P. The specific algorithms used to predict subsequent, expected-to-be-stored waveform-specific area data are called Kalman equations. For a discussion of the Kalman equations necessary to second artifact rejection technique 42, see Geld, Arthur, *Applied Optimal Estimation*, MIT Press, 1974. By using the Kalman Equations set out in *Applied Optimal Estimation*, a second artifact rejection technique program directs the microprocessor to predict value 78P based on a prediction curve that microprocessor 31 generates from area data values 74, 76.

Then, the second artifact rejection technique program directs the microprocessor to set upper and lower bounds for predicted waveform-specific area data value 78P. These bounds are shown by upper bound bar 78UB and lower bound bar 78LB. Next, the microprocessor develops a waveform integral 78I of pulsation waveform 78a (depicted in FIG. 8A). Then, microprocessor 31 checks, under the direction of soon-to-be-described portion of program 300, whether developed waveform integral 78I is within upper bounds 78UB and lower bounds 78LB.

As shown in FIG. 8B, second waveform area data evaluator 38 accepts waveform-specific area data value 78I because it falls within upper bounds 78UB and lower bounds 78LB.

Next, second artifact rejection technique program directs the microprocessor to calculate updated area data value 78U based on the difference between waveform integral 78I and predicted area data value 78P. Further, the microprocessor adjusts area data values 74I, 76I so that a first (undepicted) smoothed curve is generated through adjusted waveform-specific area data values $74A_1$, $76A_1$, and updated waveform-specific area data value 78U.

Next, the microprocessor repeats the process for cuff counterpressure level 80. Again, the microprocessor, under the direction of the second artifact rejection technique program accepts a developed waveform integral 80I because it falls within upper bounds 80UB and lower bounds 80LB of predicted, expected-to-be-stored waveform-specific area data value 80P. Then, the microprocessor calculates an updated area data value 80U, and adjusts once-adjusted area data values 74A, 76A, of counterpressure levels 74, 76 to twice-adjusted area data values $74A_2$, $76A_2$. Also, the microprocessor adjusts value 78I to value $78A_1$. Finally, the microprocessor generates a second (undepicted) adjusted curve through points $74A_2$, $76A_2$, and $78A_1$.

Next, the microprocessor predicts a subsequent, expected-to-be-stored waveform-specific area data value 82P for cuff counterpressure level 82. However, the microprocessor does not accept developed waveform integral 82I because it is outside upper bound 82UB of predicted waveform-specific area data value 82P.

Referring back to FIG. 8A, the microprocessor then develops an integral of second waveform 82b at counterpressure level 82. Further, the microprocessor checks whether the developed integral of waveform 82b was within bounds 82UB, 82LB. If, as shown in the first scenario of FIG. 8A at counterpressure level 82, waveform 82B was processed, and its developed integral was within bounds 82UB, 82LB, then microprocessor directs valve 22 to decrease counterpressure to next level 84.

However, if the second scenario depicted at counterpressure level 82 and FIG. A occurred, then the microprocessor rejects developed integrals of pulsation waveforms 82C–82E because they are outside bounds 82UB, 82LB.

Next, the portion of program 300 that directs the microprocessor to determine a final area data value for the third and subsequent counterpressure levels (shown in FIG. 8A as levels 78–86) will be described. Thus, turning to FIG. 9, attention is directed to decision block 358 (D16) which is the decision block the microprocessor is directed to if counterpressure is at the third or subsequent counterpressure levels.

Referring to FIG. 9, decision block 358 (D16) asks whether a waveform integral developed by the microprocessor for a pulsation waveform is less than or equal to the upper bounds of the present counterpressure level's predicted waveform-specific area data value. In order to graphically depict what decision block 358 (D16) concerns, reference is made to the discussion of predicted waveform-specific area data value 78P of cuff counterpressure level 78 depicted in FIG. 9B. Thus, the reference to a predicted area data value and the upper bounds of a predicted area data value in decision block 358 (D16) refers to values 78P and 78UB of FIG. 9B.

If the answer to decision block 358 (D16) is no, then task block 360 (T13) labels the program for Waveform Beginning Program 200 and the program exits to Kernel so that microprocessor 31 will monitor a next blood pressure induced waveform at the same, present counterpressure level. Again, reference is made to FIG. 8B and FIG. 8A. Specifically, referring to counterpressure level 82, the microprocessor processes waveform 82A of FIG. 8A and develops a waveform integral represented by point 82I of FIG. 8B. Further, integral 82I is outside upper bounds 82UB of predicted area data value 82P. This, event graphically depicts what happens when the answer to decision block 358 (D16) is no. Thus, task block 360 (T13) labels the program for Waveform Beginning Program 200 so that a next waveform will be processed at counterpressure level 82. This next waveform is shown as waveform 82B of FIG. 8A.

Continuing with the discussion of decision block 358 (D16), if the answer to decision block 358 (D16) is yes, then decision block 362 (D17) asks whether the present, developed waveform integral is greater than or equal to the lower bounds of the present counterpressure level's predicted area data value. If the answer to decision block 362 (D17) is no, then task block 360 (T13) again labels the program for Waveform Beginning Program 200 and the program exits to Kernel so that microprocessor 31 will process a next pulsation waveform at the present counterpressure level. Again, reference is made to FIG. 8B, and specifically to lower bounds 78LB of predicted waveform-specific area data value 78P of cuff counterpressure level 78 for an example of the lower bounds criterion represented in decision block 362 (D17).

If the answer to decision block 362 (D17) is yes, then the developed waveform integral for the present counterpressure level is accepted. Thus, task block 364 (T14) stores the integral as the waveform-specific area data value for the counterpressure level, and task block 366 (T15) stores the corresponding counterpressure level value at which the pulsation waveform represented by the integral occurred. Finally, task block 368 (T16) labels the program ready for a next counterpressure level and the program exits to Kernel 308 so that microprocessor 31 will signal pressure control 44 to decrease counterpressure by a next increment of 5½-mm Hg.

Turning now to FIG. 8C, a second fragmented graph of waveform-specific area data vs. cuff counterpressure levels is shown wherein corresponding predicted, developed, updated, and adjusted waveform-specific area data values are calculated and developed by the process outlined in the discussion of FIG. 9B. According to the preferred method of practicing the present invention, the microprocessor adjusts waveform-specific area data values for counterpressure levels relative to a present counterpressure level.

The adjustment is made in "forward"- and "backward"-looking fashion. Thus, area data values for previous counterpressure levels are adjusted ("backward-looking"), and a predicted area data value for a next, yet-to-be-monitored counterpressure level is adjusted ("forward-looking"). While different numbers of area data values can be chosen for adjustment treatment, say in the range of about three to five, in the method disclosed herein, five previous counterpressure levels are adjusted.

For a discussion of the algorithms that are used in the invention to direct the microprocessor's data adjustments, see the discussion of fixed lag smoothing in Ch. 7.3 of Anderson and Moore, *Optimal Filtering*, Prentice Hall, 1979.

Thus, for example, when the second artifact rejection technique program directs the microprocessor to calculate an updated waveform-specific area data value 88U for cuff counterpressure level 88, the microprocessor adjusts the area data values of the five previous counterpressure levels 78, 80, 82, 84, 86. Therefore, adjusted waveform-specific area data value $78A_5$ is the final waveform-specific area data value for counterpressure level 78.

Further, adjusted waveform-specific area data values $74A_4$ and $76A_5$ are the final waveform-specific area data values for counterpressure levels 74, 76, respectively. Thus, the microprocessor generates a fifth adjusted curve 94 connecting all final waveform-specific area data values. In FIG. 9C, the fifth adjusted curve is partially shown by dot-dashed lines connecting final waveform-specific area data values $74A_4$, $76A_5$, and $78A_5$.

Turning now to FIG. 8D, a graph of waveform-specific area data vs. cuff counterpressure levels for the entire measurement cycle of living test subject 18 is shown. After monitoring the ending counterpressure level, the microprocessor generates fifth adjusted curve 94 for the final waveform-specific area data values of each counterpressure level monitored. For example, fifth adjusted curve 94 passes through final waveform-specific area data values $74A_4$, $76A_5$, and $78A_5$ of counterpressure levels 74, 76, 78, respectively.

Next, the microprocessor is directed by a program to determine desired blood pressure parameters by what has previously been described as determiner 48. First, the microprocessor determines MAP as the lowest counterpressure level with the greatest final area data value. Further, the microprocessor determines the systolic and diastolic pressure of subject 18 as the counterpressure levels corresponding to waveform-specific area data values of fifth adjusted curve 94 that have an experimentally determined fractional relationship with the greatest area data value corresponding to MAP.

The preferred practice of the present invention determines systolic pressure as the counterpressure level above MAP corresponding to the waveform-specific area data value on fifth adjusted curve 94 that is sixty percent of the MAP waveform-specific area data value. Further, the preferred practice of the present invention determines the diastolic pressure of subject 18 as the waveform-specific area data value corresponding to a counterpressure level below MAP wherein the area data value on fifth adjusted curve 94 is eighty percent of the value of the MAP waveform-specific area data value.

While a preferred method of practicing the invention has been disclosed, it should be appreciated that variations and modifications may be made thereto without departing from the spirit of the invention.

It is claimed and desired to secure by Letters Patent:

1. A noninvasive, oscillometric blood-pressure measurement method to determine blood-pressure parameters derived from data acquired relative to blood-pressure-induced pressure waveforms, said method enabling the acquisition of such data with improved accuracy and an improved faster rate, and said method, in operative condition relative to a blood vessel in a living subject, comprising establishing in a means for producing a baseline counterpressure adjacent such vessel a predetermined beginning counterpressure above systolic pressure, thus to occlude the vessel, progressively reducing counterpressure in steps from a beginning counterpressure step to a predetermined ending counterpressure step, during said reducing, and on a step-by-step basis, monitoring the waveforms of blood-pressure-induced changes in the pressure in such means, on the basis of said step-by-step monitoring, developing and storing waveform-specific partial-area data, and from such stored data, calculating the desired parameters.

2. The method of claim 1, wherein said monitoring includes sampling, during the occurrence of each waveform, recurrently, the instantaneous level of pressure in such means and performing a first artifact-rejection technique to confirm the validity of each sample, said first technique being conducted utilizing predetermined criteria established in light of a previously noted sample, and said developing includes conducting, with respect to successive validation-confirmed samples, a running waveform-specific area-data integration for each of such waveforms.

3. The method of claim 2 wherein, with respect to each waveform from which validated samples result in the storing of waveform-specific area data, the conducting of integration takes place with respect to validated samples that extend at least to the point where the waveform reaches a maximum amplitude.

4. The method of claim 2, wherein said performing employs waveform slope prediction to establish such predetermined criteria.

5. The method of claim 4, wherein such predetermined criteria include a first type that are used relative to samples representing a first segment of such waveforms, and a second type that are used relative to samples representing a second segment of such waveforms.

6. The method of claims 2, 3, 4 or 5, wherein said developing further includes performing a second artifact-rejection technique which utilizes previously stored waveform-specific area data to produce a curve that predicts subsequent, expected-to-be-stored waveform-specific area data.

7. The method of claim 6, wherein the production of such curve includes the generation of an associated acceptance window which includes lower and upper boundaries.

8. The method of claim 6, wherein such second artifact-rejection technique performed in said developing further includes utilizing subsequent, developed waveform-specific area data to adjust previously stored waveform-specific area data.

9. A noninvasive, oscillometric blood-pressure measurement method to determine blood-pressure parameters derived from data acquired relative to blood-pressure-induced pressure waveforms, said method promoting the rapid acquisition and verification of such data, and in operative condition relative to a blood vessel in a living subject, comprising establishing in a means for producing a baseline counterpressure adjacent such vessel a predetermined beginning counterpressure above systolic pressure, thus to occlude the vessel, progressively reducing counterpressure in steps from a beginning counterpressure step to a predetermined ending counterpressure step, during said reducing, monitoring the waveforms of blood-pressure-induced changes in the pressure in such means, on the basis of said monitoring, developing and storing waveform-specific partial-area data, and determining from such data:

(a) means arterial pressure to the lowest baseline counterpressure corresponding in time with occurrence of the blood-pressure waveform associated with the largest area-data value;

(b) systolic pressure to be the baseline counterpressure corresponding in time with occurrence of the blood-pressure waveform whose associated area-data value has a first predetermined fractional relationship with the value identified above in subparagraph (a); and (c) diastolic pressure to be the baseline counterpressure corresponding in time with occurrence of the blood-pressure waveform whose associated area-data value has a second predetermined fractional relationship with the value identified above in subparagraph (a).

10. The method of claim 9, wherein said monitoring includes sampling during the occurrence of each waveform, recurrently, the instantaneous level of pressure in such means and performing a first artifact-rejection technique to confirm the validity of each sample, said first technique being conducted by utilizing predetermined criteria established in light of a previous noted sample, and said developing includes conducting, with respect to successive validation-confirmed samples, a running waveform-specific area-data integration for each of such waveforms.

11. The method of claim 10 wherein, with respect to each waveform from which validated samples result in the storing of waveform-specific area data, the conducting of integration takes place with respect to validated samples that extend at least to the point where the waveform reaches a maximum amplitude.

12. The method of claim 10, wherein said performing employs waveform slope prediction to establish such predetermined criteria.

13. The method of claim 12, wherein such predetermined criteria include a first type that are used relative to samples representing a first segment of such waveforms, and a second type that are used relative to samples representing a second segment of such waveforms.

14. The method of claims 10, 11, 12 or 13, wherein said developing further includes performing a second artifact-rejection technique which utilizes previously stored waveform-specific area data to produce a curve that predicts subsequent, expected-to-be-stored waveform-specific area data.

15. The method of claim 14, wherein the production of such curve includes the generation of an associated acceptance window which includes lower and upper boundaries.

16. The method of claim 14, wherein such second artifact-rejection technique performed in said developing further includes utilizing subsequent, developed waveform-specific area data to adjust previously stored waveform-specific area data.

17. An artifact-rejection method to be used with noninvasive blood-pressure measuring apparatus that determines blood-pressure parameters derived from data acquired relative to blood-pressure-induced pressure waveforms, said method comprising:

in a means for producing a baseline counterpressure adjacent a blood vessel in a living subject, progressively reducing such counterpressure in counterpressure steps from a predetermined beginning, occluding baseline counterpressure above systolic pressure to a predetermined ending baseline counterpressure;

during said reducing, and for a predetermined number of such counterpressure steps, and at each such step, monitoring a plurality of the waveforms of blood-pressure-induced changes in the pressure of such means;

on the basis of said monitoring, developing and storing waveform-specific area data;

at each of such counterpressure steps, choosing a predetermined number of stored, waveform-specific area-data values as indicative of blood pressure and computing an average waveform-specific area value from such chosen values;

thereafter, from such average values, fitting a curve and, from such curve, predicting an expected-to-be-stored waveform-specific area-data value for a next baseline counterpressure step, and applying experimentally determined bounds to such expected-to-be-stored waveform-specific area-data value;

modifying said monitoring at such next baseline counterpressure step so that a single waveform-specific area-data value is developed and stored; and checking whether such single value is within such bounds from said predicting as a way of determining the acceptability of the value.

18. The method of claim 17, wherein said checking includes, if such single value is outside of such bounds, staying at such next counterpressure step, and repeating said monitoring, integrating, and checking, and if such single value is within such bounds, accepting such single value, and repeating said modifying step at a next counterpressure step.

19. An artifact-rejection method to be used with noninvasive blood-pressure measuring apparatus that processes two streams of data corresponding to blood-pressure-induced pressure waveforms, said method comprising:

in a means for producing a baseline counterpressure adjacent a blood vessel in a living subject, progressively reducing such counterpressure in counterpressure steps from a predetermined beginning, blood-vessel-occluding, baseline-counterpressure step above systolic pressure to an ending baseline counterpressure step;

during said reducing, and at each such counterpressure step, monitoring at least one waveform of blood-pressure-induced changes in the pressure within such means;

said monitoring including, for each such waveform, acquiring two streams of data, the first such stream corresponding to baseline counterpressure data, and the second such stream corresponding to blood-pressure-induced, pressure-pulsation data, viewing such data in three different phases of activity; and from said viewing, verifying that such waveform is blood-pressure-induced by checking the first such data-phase according to a first, predetermined verification criteria, by checking the second such phase according to a second, predetermined verification criteria, and by checking the third such phase according to a third, predetermined verification criteria.

20. The method of claim 19, wherein such waveform is characterized by the second stream going from a beginning divergence point, relative to the first such stream, to a maximum point of divergence, and by then converging back on the first stream, and the first such phase is characterized by a first divergence parameter, the second such phase is characterized by a second divergence parameter, and the third such phase is characterized by a first convergence parameter.

* * * * *